US009119682B2

(12) United States Patent
Stoll et al.

(10) Patent No.: US 9,119,682 B2
(45) Date of Patent: Sep. 1, 2015

(54) BONE PLATING SYSTEM AND METHOD

(75) Inventors: Caleb Stoll, Broomfield, CO (US);
Morgan Lorio, Bristol, TN (US);
Michael Fulton, Superior, CO (US)

(73) Assignee: LANX, INC., Broomfield, CO (US)

(*) Notice: Subject to any disclaimer, the term of this patent is extended or adjusted under 35 U.S.C. 154(b) by 337 days.

(21) Appl. No.: 13/580,611

(22) PCT Filed: Mar. 3, 2011

(86) PCT No.: PCT/US2011/027013
§ 371 (c)(1),
(2), (4) Date: Nov. 5, 2012

(87) PCT Pub. No.: WO2011/109610
PCT Pub. Date: Sep. 9, 2011

(65) Prior Publication Data
US 2013/0053895 A1    Feb. 28, 2013

Related U.S. Application Data

(60) Provisional application No. 61/310,007, filed on Mar. 3, 2010.

(51) Int. Cl.
A61B 17/56    (2006.01)
A61B 17/80    (2006.01)
A61B 17/70    (2006.01)

(52) U.S. Cl.
CPC .......... *A61B 17/8042* (2013.01); *A61B 17/809* (2013.01); *A61B 17/8028* (2013.01); *A61B 17/7059* (2013.01)

(58) Field of Classification Search
CPC ............... A61B 17/80; A61B 17/8028; A61B 17/8061; A61B 17/8042

USPC .............................. 606/280–286, 70–71, 293
See application file for complete search history.

(56) References Cited

U.S. PATENT DOCUMENTS

| 5,002,544 | A  | * | 3/1991  | Klaue et al. ................. 606/280 |
| 5,062,850 | A  | * | 11/1991 | MacMillan et al. ....... 623/17.11 |
| 5,474,553 | A  | * | 12/1995 | Baumgart ........................ 606/71 |
| 5,486,176 | A  | * | 1/1996  | Hildebrand et al. ............ 606/71 |
| 5,741,257 | A  | * | 4/1998  | Kirsch ........................... 606/281 |
| 6,187,053 | B1 | * | 2/2001  | Minuth ........................... 128/898 |
| 6,336,930 | B1 | * | 1/2002  | Stalcup et al. ................ 606/284 |
| 6,663,632 | B1 | * | 12/2003 | Frigg .............................. 606/246 |
| 7,666,185 | B2 | * | 2/2010  | Ryan et al. ...................... 606/71 |
| 7,815,681 | B2 | * | 10/2010 | Ferguson ..................... 623/17.16 |

(Continued)

OTHER PUBLICATIONS

Notification of Transmittal of the International Search Report and the Written Opinion of the International Searching Authority, or the Declaration, date of mailing Nov. 25, 2011.

*Primary Examiner* — Eduardo C Robert
*Assistant Examiner* — Stuart S Bray
(74) *Attorney, Agent, or Firm* — Schwegman Lundberg & Woessner, P.A.

(57) ABSTRACT

The described apparatus and method include a bone plating system comprising a plate longitudinally extending between a first plate end and a second plate end, wherein the plate further comprises a first plate surface spaced apart from an opposing second plate surface. Further, the bone plating system further includes a first spacer segment longitudinally extending between a first spacer end and a second spacer end, wherein the first spacer segment is shaped to adapt the plate to conform to an adjacent bone segment surface.

22 Claims, 17 Drawing Sheets

(56) References Cited

U.S. PATENT DOCUMENTS

| | | | |
|---|---|---|---|
| 7,981,141 B2* | 7/2011 | Morrison et al. | 606/281 |
| 8,002,808 B2* | 8/2011 | Morrison et al. | 606/280 |
| 8,057,521 B2* | 11/2011 | Smisson et al. | 606/288 |
| 8,128,628 B2* | 3/2012 | Freid et al. | 606/71 |
| 8,262,659 B2* | 9/2012 | Ryan et al. | 606/71 |
| 8,328,853 B2* | 12/2012 | Ibrahim et al. | 606/282 |
| 8,574,270 B2* | 11/2013 | Hess et al. | 606/282 |
| 8,784,458 B1* | 7/2014 | White et al. | 606/288 |
| 8,814,869 B2* | 8/2014 | Freid et al. | 606/71 |
| 8,814,912 B2* | 8/2014 | Carlson et al. | 606/264 |
| 2004/0102773 A1* | 5/2004 | Morrison et al. | 606/61 |
| 2005/0049595 A1* | 3/2005 | Suh et al. | 606/69 |
| 2006/0036250 A1* | 2/2006 | Lange et al. | 606/69 |
| 2006/0116683 A1* | 6/2006 | Barrall et al. | 606/71 |
| 2006/0122605 A1* | 6/2006 | Suh et al. | 606/69 |
| 2006/0149254 A1* | 7/2006 | Lauryssen et al. | 606/69 |
| 2006/0200134 A1* | 9/2006 | Freid et al. | 606/61 |
| 2006/0235409 A1* | 10/2006 | Blain | 606/71 |
| 2009/0171396 A1* | 7/2009 | Baynham et al. | 606/280 |
| 2010/0082029 A1* | 4/2010 | Ibrahim et al. | 606/71 |
| 2010/0121329 A1* | 5/2010 | Ryan et al. | 606/71 |
| 2012/0283782 A1* | 11/2012 | Ryan et al. | 606/279 |
| 2013/0165934 A1* | 6/2013 | Ibrahim et al. | 606/71 |

* cited by examiner

BONE PLATING SYSTEM AND METHOD

FIELD OF THE INVENTION

The invention relates to plating systems for stabilizing, bone and associated methods, and more particularly, to spinal plating systems and methods.

BACKGROUND

Plating devices and systems are often used to secure adjacent bone segments. For example, plating devices and systems may be used to stabilize fractured or adjacent bone segments, such as relatively straight bones or adjacent vertebrae in the spine, and/or to hold the bone segments together to allow the bone segments to fuse together. Further, for instance, in spinal applications, a plating device may be used in combination with an implant positioned between the vertebrae to fuse to the vertebrae. The fixating and fusion of bone is also known as osteosynthesis.

In any case, the anatomy of each individual may vary, either naturally or as a result of a disease or defect, such as spondylolisthesis. As a result, the surfaces of adjacent bone segments may also vary, thereby creating a mismatch between a portion of a bottom surface of the plating device and the corresponding surface of the adjacent bone segment. For example, in spinal applications, the anterior surface of the L5 vertebra is displaced relative to the anterior surface of the S1 vertebra by a promontory angle, which is generally an acute angle. As such, screws used to affix the plate to the adjacent bone segment must span a gap caused by the mismatch, thereby creating instability between the plate and the bone segment.

Thus, based on the foregoing, improved plating devices and systems are desired.

SUMMARY

The described aspects provide, a bone plating system, a surgical set and a method of bone stabilization that includes a plate and a removably attachable spacer segment, such that the spacer segment adapts the plate to conform to the particular anatomy of a given patient for hone stabilization.

In one aspect, a bone plating system comprises a plate longitudinally extending between a first plate end and a second plate end, wherein the plate further comprises a first plate surface spaced apart from an opposing second plate surface. Further, the hone plating system includes a cover attachable to the plate to retain fasteners from dissociating from the plate.

In another aspect, a bone plating system comprises a plate longitudinally extending between a first plate end and a second plate end, wherein the plate further comprises a first plate surface spaced apart front an opposing second plate surface. Further, the bone plating system further includes a first spacer segment longitudinally extending between as first spacer end and a second spacer end, wherein the first spacer segment is shaped to adapt the plate to conform to an adjacent bone segment surface In another aspect, a method of fixating bone segments comprises obtaining a plate, obtaining a spacer segment shaped to adapt the plate to conform to an adjacent bone segment surface, and combining the plate and the spacer segment.

BRIEF DESCRIPTION OF THE DRAWINGS

Various examples of the described aspects will be discussed with reference to the appended drawings. These drawings depict only illustrative examples of the invention and are not to be considered limiting of its scope.

FIG. 41 is a sectional view taken along lie 43-43 of FIG. 42.

DESCRIPTION OF THE ILLUSTRATIVE EXAMPLES

Figure 1:
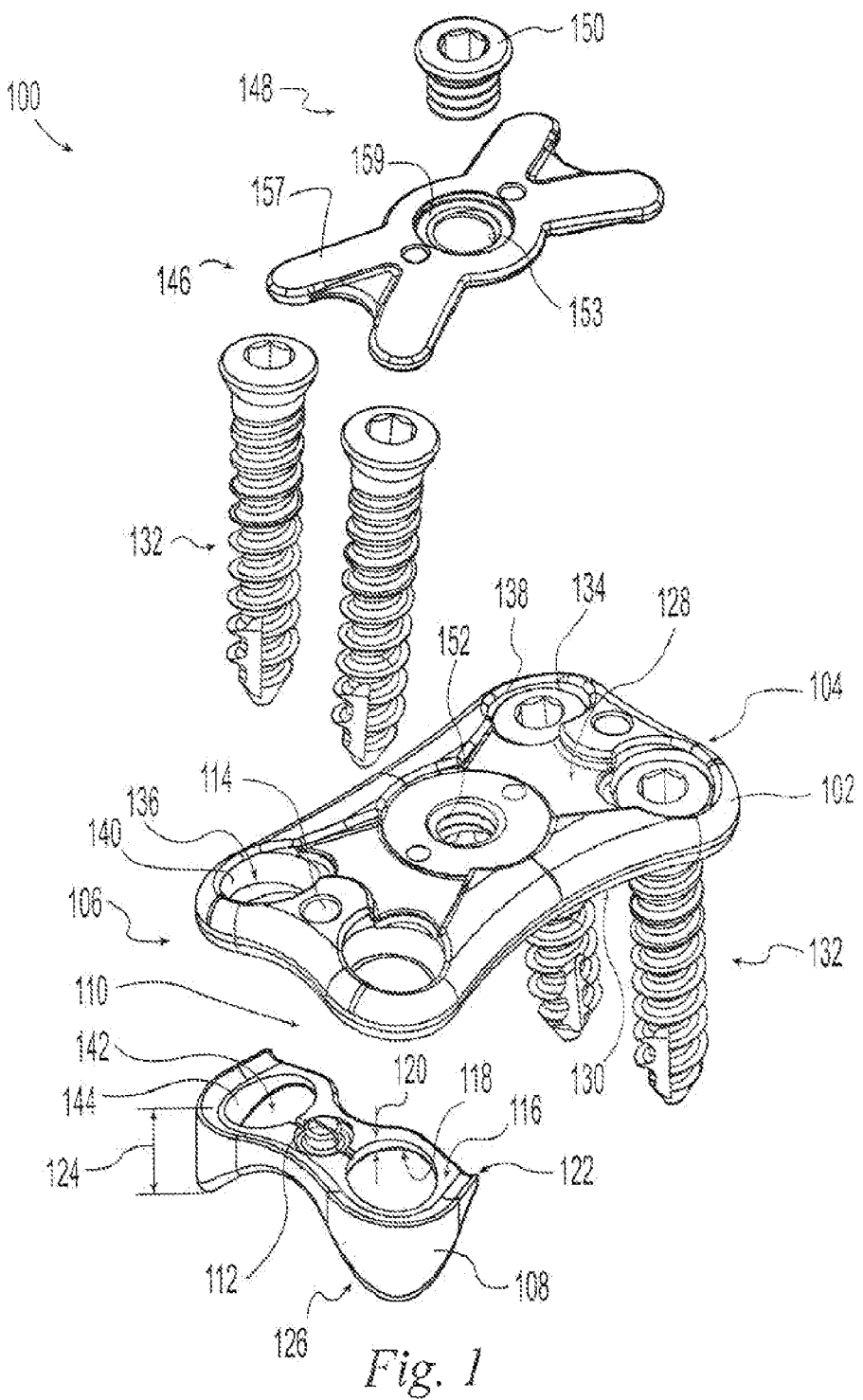
FIG. 1 is an exploded view of an aspect of a bone plating system.

Referring to FIGS. 1-7, in an aspect, a bone plating system 100 includes a plate 102 having a first plate end 104 and an opposite a second plate end 106, and at least one spacer segment 108 removably securable to plate 102. Spacer segment 108 is sized or shaped, or both, to adapt plate 102 to conform to a surface of an adjacent one segment. Optionally, bone plating system 100 may include a connector 110 configured to releasably secure spacer segment 108 to plate 102. For example, in an aspect, connector 110 may include a first connector portion 112 on spacer segment 108 and a corresponding second connector portion 114 on plate 102, wherein first connector portion 112 and second connector portion 114 interact to allow spacer segment 108 to be attached to or detached from plate 102. It should be noted that in aspects, system 100 may include multiple spacer segments, with spacer segments connected at various locations as described below relative, to various aspects of the disclosure.

Spacer segment 108 further comprises a first spacer surface 116 spaced apart from an opposing second spacer surface 118 to define a spacer thickness. In some optional aspects, the spacer thickness may not be uniform, but may be different at different ends or at different sides, or may be variable across an entirety of spacer segment 108, or some combination thereof. For example, in an aspect, the spacer thickness may include a first spacer thickness 120 at a first spacer end 122 and a second spacer thickness 124 at or adjacent to at least a portion of an opposite second spacer end 126. In some aspects, spacer segment 108 has different thicknesses at or adjacent to each end. For example, second spacer thickness 124 may have a site greater than first spacer thickness 120. In this case, for example, second spacer thickness 124 is positioned at an end of spacer segment 108 that is aligned with an end of plate 102. For instance, with plate 102 having a first plate surface 128 and an opposing second plate surface 130, and with spacer segment 108 secured to second plate surface 130 at second plate end 106 such that second spacer end 126 is aligned with second plate end 106, second spacer thickness 124 is sized to substantially match or fill a gap between second plate surface 130 and a surface of an adjacent bone segment to which second plate end 106 is to be secured. In another example, first spacer thickness 120 may have a size greater than second spacer thickness 124. For example, in this case, first spacer thickness 120 may be positioned at an end of spacer segment 108 that is positioned toward a center of plate 102, for example, to aid in indexing a position of plate 102 relative to an adjacent bone segment, or to support plate 102 relative to an adjacent bone segment and relieve forces on bone screws holding plate 102 to the adjacent bone segment, as is discussed in more detail below with respect to FIGS. 20-29. In any case, however, spacer segment 108 has a size or shape, or some combination of both, to adapt plate 102 to conform to adjacent bone segments, or to allow spacer segment 108 in combination with plate 102 to support a relative positioning between adjacent bone segments, or both.

With regard to the securing of plate 102 and spacer segment 108 to adjacent bone segments, optionally, in addition to plate 102, spacer segment 108 and connector 110, system 100 may further include a plurality of securing mechanisms 132, such as bone screws, configured to partially pass through corresponding through-holes 134 and 136 and fix plate 102 to the respective adjacent bone segment(s). Through-holes 134 and 136 are respectively defined by internal walls 138 and 140 between plate surfaces 128 and 130 at plate ends 104 and 106. Further, in some aspects, spacer segment 108 may additionally include one or more through-holes 142 defined by a wall 144 between spacer surfaces 116 and 118, wherein the respective securing mechanisms 132 are configured to pass partially through one or more through-holes 142 to fix spacer segment 108 between plate 102 and the adjacent one segment. It should be noted, however, that in other aspects, spacer segment 108 may not include through-holes 142, or may include wall 144 as part of an exterior surface of spacer segment 108, e.g. such that wall 144 does not entirely encompass securing mechanism 132. Additionally, in some aspects, the plurality of securing mechanisms 132 include different sets of securing mechanisms having different lengths or different thread patterns, or both, for example, to allow for adjustments between varying anatomy to ensure the securing mechanisms sufficiently engage the bone segments. It should be understood, however, that securing mechanism 132 may include not only a screw, but any other mechanism or component configured to attach plate 102 and/or spacer segment 108 to bone, such as an adhesive, a rivet, a tie, etc.

Also optionally, in addition to plate 102, spacer segment 108 and connector 110, or in addition to plate 102, spacer segment 108, connector 110 and securing mechanisms 132, system 100 may further include a cover plate 146 removably securable to plate 102, such as through securing mechanism 148. For example. In an aspect, securing mechanism 148 may include a first securing portion 150, such as a screw, and a corresponding second securing portion 152, such as a threaded wall defining a cavity in plate 102, wherein first securing portion 150 and second securing portion 152 interact to allow cover plate 146 to be attached to or unattached from plate 102. Optionally in sire aspects, securing mechanism 148 may additionally include a third securing portion 153 in cover plate 146, such as corresponding screw threads. It should be understood, however, that securing mechanism 14S may include not only screws, but any other mechanism or component configured to attach cover plate 146 to plate 102, such as a snap-fit or, force-fit connector, an adhesive, a rivet, a tie, etc.

Figure 7:
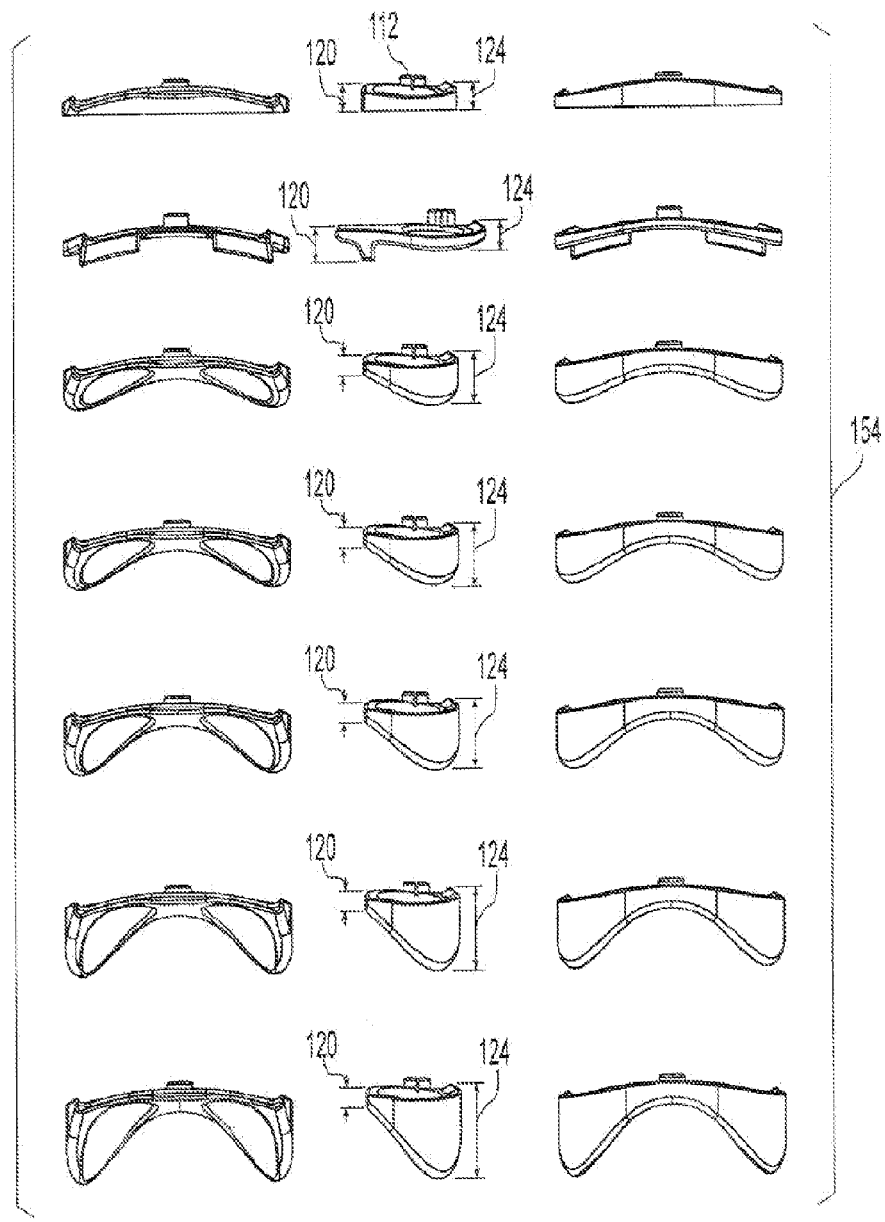
FIG. 7 is a respective series of front end views, side views, and rear end views of a plurality of spacer segments of FIG. 1, with each of the respective space segments having a different size and/or shape.
Figure 8:
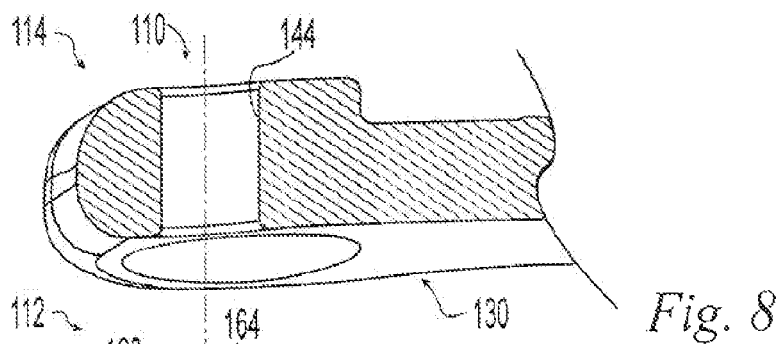
FIGS. 8-12 are partial cross-sectional views of an aspect of a connector of FIG. 1.
Figure 9:
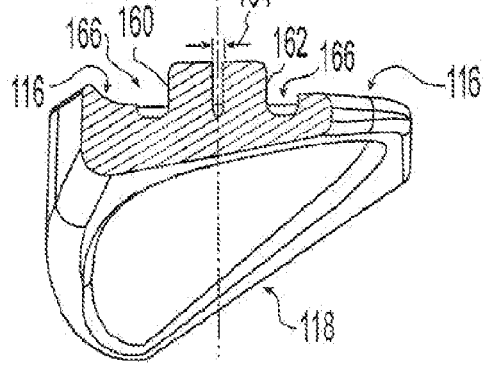
Figure 10:
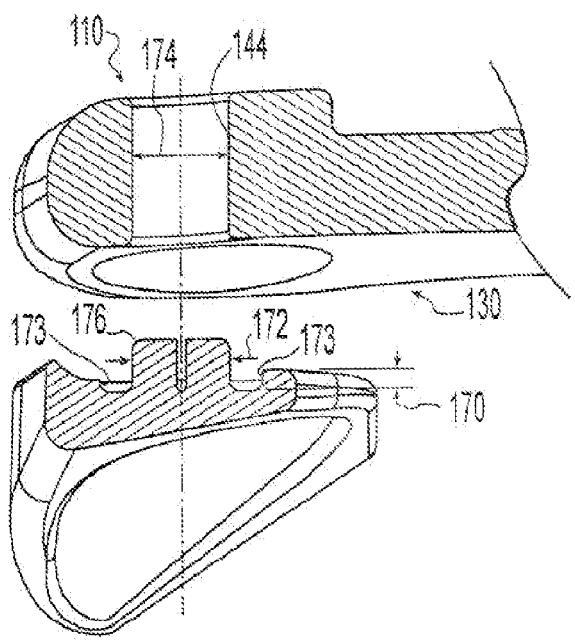
Figure 10:
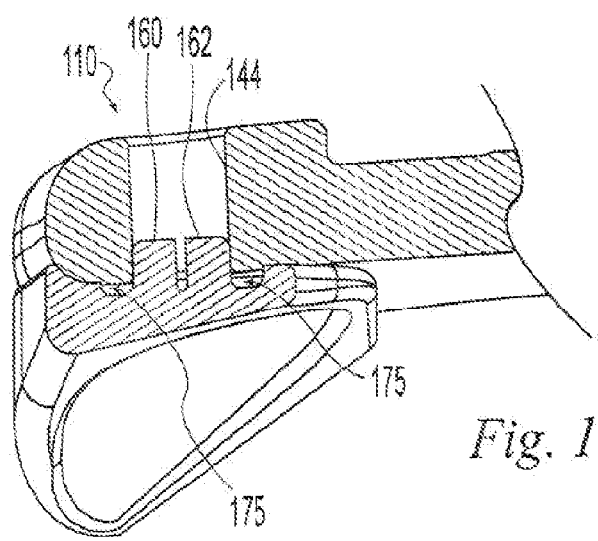

Moreover, referring specifically to FIGS. 1 and 7, spacer segment 108 may be selected from a plurality of spacer segments 154 that are interchangeable, but where each of the plurality of spacer segments 154 has a different size or shape or a combination of both. Further, for instance, each of the plurality of spacer segments 154 may have or include a same or a different shape, such as, but not limited to, shapes including a wedge, a claw, a flat, a ledge or projection, a shim, a relatively conforming shape for stacking, and further shapes disclosed herein, or any combination of these shapes. As such, system 100 allows the selected spacer segment, such as spacer segment 108, to be sized or shaped, or both, to most closely match a size or shape, or both, of a mismatch between second plate surface 130 at the bone segment to which second plate end 106 is configured to be secured when plate 102 is positioned again the respective surfaces of the adjacent bone segments. For example, in a spinal application, first plate end 104 may be secured to an anterior surface of an L5 vertebra, while second plate end 106 and spacer segment 108 may be secured to an anterior surface of an adjacent S1 vertebra, and spacer segment 108 substantially fills a gap defined by a displacement between the surfaces of the L5 and S1 vertebrae, for example, such as a gap produced by the promontory angle. Other applications of bone plating system 100 may include, but are not limited to, adapting plate 102 to conform to a variation due to spondylosis, spondylolisthesis, bone or spinal malformations, a bone segment having an osteophyte, a natural anatomical variation, a genetic or injury-induced variation, a man-made variation, or any other cause of mismatch between a bottom of plate 102 and an adjacent bone segment to which plate 102 is to be attached.

Additionally, in an optional aspect, the plurality of spacer segments 154 may be interchangeable based on having a same first connector portion 112, thereby enabling the respective spacer segment to be secured to the same second connector portion 114 of plate 102 to define connector 110. Moreover, the plurality of spacer segments 154 may be interchangeable, such as by having a same shape on the surface or surfaces positioned against plate 102, such as first spacer surface 116, or by utilizing a same connector 110, or both.

Thus, bone plating system 100 provides at least one spacer segment 108 combinable with plate 102 to provide a boneadjoining surface that substantially conforms to, or that supports a relative positioning of, or that provides an indexed position of plate 102 relative to, adjacent bone segments to which plate 102 and spacer segment(s) 108 are secured, such as for stabilizing the adjacent bone segments. Further, in some optional aspects, at least one portion of spacer segment 108 may have a thickness greater than another portion of spacer segment 108, thereby allowing spacer segment 108 to fill a gap between plate 102 and a respective bone segment when plate 102 is placed in position to be secured to the adjacent bone segments, or in other aspects to maintain a relative position between the adjacent bone segments when plate 102 is placed in position to be secured to the adjacent bone segments, or in other aspects to provides an indexed position to locate plate 102 relative to bone segment, or any combination thereof. Additionally, spacer segment 108 may be selected from a plurality of different spacer segments each having different thicknesses or sizes or shapes, or any combination thereof, thereby providing flexibility during a surgical procedure to adapt a combination of plate 102 and spacer segment 108 that sufficiently mates or aligns with the given anatomy.

Figure 5:
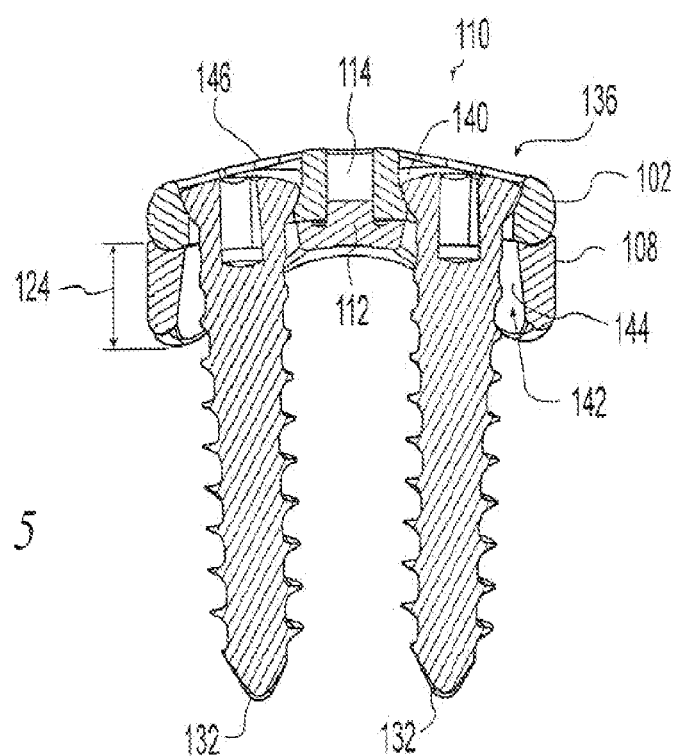
FIG. 5 is a cross-section view along line 5-5 of FIG. 4.
Figure 6:
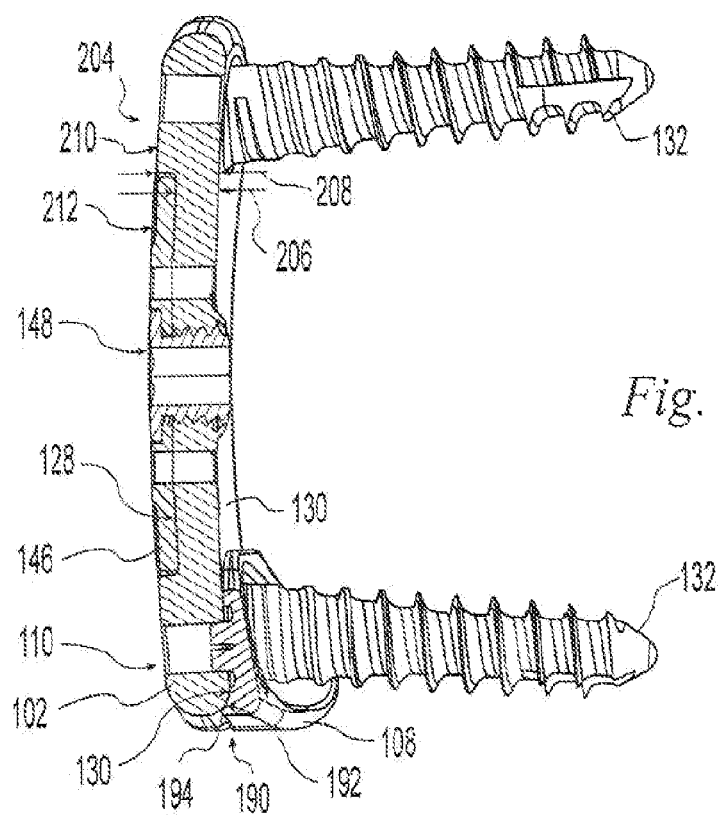
FIG. 6 is a cross-section view along line 6-6 of FIG. 4.

Referring more specifically to FIGS. 1, 5 and 6, in some optional aspects, system 100 may include connector 110, such as a snap-fit type, or quick connect and release type, of removable securing mechanism. As utilized herein, it should be understood that snap-fit type, or quick connect and release type, of removable securing mechanism comprises any type of mechanism that allows a relatively fast, such as on the order of about a couple of seconds, connection or release of spacer segment 108 to or from plate 102. Further, for example, in an aspect, a snap-fit type or quick connect and release type of connector 110 is configured to connect or disconnect spacer segment 108 and plate 102 through hand-actuation or with one or more tools creating forces substantially equivalent to a hand-actuated tool, it should be noted, however, that connector 110 may include any type of mechanism or structure that allows spacer segment 108 to be secured to plate 102. For instance, other aspects of connector 110 may include, but are not limited to, mechanism or structures such as a force-fit connector, a screw mechanism, a keyed connector, a corresponding tenon and mortise, a splined connector, an adhesive, a dovetail connection, a sliding fit, a press fit, a keyed spline, a snap fit, or a screwed or threaded connection. In still further aspects, connector 110 may provide a conforming functionality, but not a fixing functionality, whereby a portion of spacer segment 108 may be shaped to cup or otherwise partially encompass a portion of plate 102. Still further, it should be noted that one or more connectors 110 may be located at any relative position on plate 102 and/or spacer segment 108.

In an aspect, for example, a snap-fit type or quick connect and release type connector 110 may be attachable or detachable via a respective attachment force or detachment force substantially normal to a plane or surface, such as second plate surface 130, of plate 102. For example, in this aspect, connector 110 may include, male and female portions that connect and disconnect, such as via a force fit or via elastic deformation.

In other aspects, for example, a snap-fit type or quick connect and release type connector 110 may be attachable or detachable via a respective attachment force or detachment force substantially parallel to a plane or surface, such as second plate surface 130, of plate 102. In this case, for example, connector 110 may comprise a key element and a key chamber respectively formed on first spacer surface 116 and second plate surface 130, such as a dovetail shape, that allows spacer segment 108 and plate 102 to be connected or released through movement substantially parallel to the plane or surface, but holds the components together in a direction substantially normal to the plane or surface. An example of a dovetail arrangement is described below in reference to FIG. 50.

Referring more specifically to FIGS. 8-14, as well as FIGS. 1, 5 and 6, in an aspect, for example, first connector portion 112 may comprise two opposing extending, portions 160 and 162 spaced apart by a distance 164 that allows portions 160 and 162 to elastically deflect relative, to internal wall 144 upon insertion of first connector portion 112 into second connector portion 114. Further, first connector portion 112 may include relief surfaces 166 and 168 adjacent to at least a part of extending portions 160 and 162, wherein relief surfaces 166 and 168 are spaced from first spacer surface 116 in the direction of second spacer surface 118. Further, relief surfaces 166 and 168 define a spacing or gap 175 between extending portions 160 and 162 and one or more inner walls 173 that allows for deflection of extending portion 160 and 162 without interfering with inner walls 173. In an aspect, relief surfaces 166 and 168 may further assist in the elastic deformation of extending portions 160 and 162 during the insertion by providing room for movement of extending portions 160 and 162, while having a sufficient spacing 170 relative to first spacer surface 116 to allow first spacer surface 116 to be positioned substantially flush with second plate surface 130. In other words, if a distance 172 between extending portions 160 and 162 of first connector portion 112 is about the same as or slightly larger than a distance 174 within second connector portion 114, then the connection between the connector portions comprises a force fit and the position of relief surfaces 166 and 168 being spaced away from first spacer surface 116 provides tin open area that allows an increase in an amount of available deflection of each extending portion 160 and 162. Further, the open space provided by relief surfaces 166 and 163 enables the part of first connector portion 112 positioned outside of second connector portion 114 to be wider than the part of first connector portion 112 positioned inside of second connector portion 114.

Further, to account for misalignment upon insertion, the distal ends of extending portions 160 and 162 may define an alignment surface 176, such as a surface that includes, at least in part an acute or angled surface, a rounded surface, a chamfer, a bevel, etc., to enable ends of extending portions 160 and 162 to align with holes defined by internal wall 144 to ease insertion.

Figure 11:
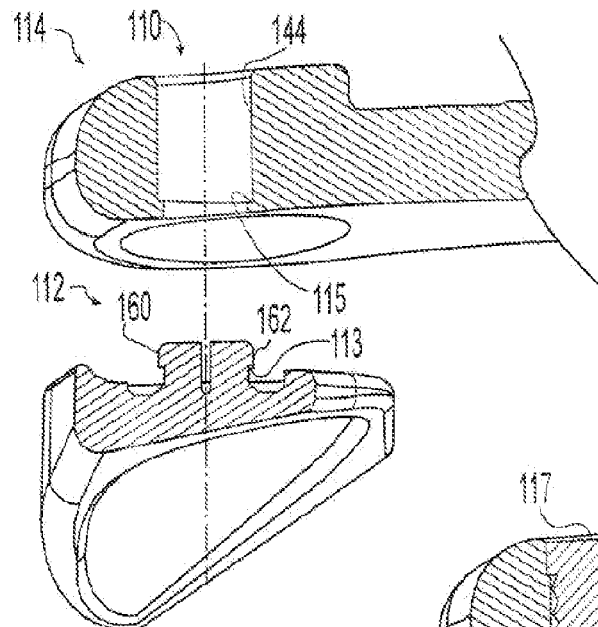
Figure 12:
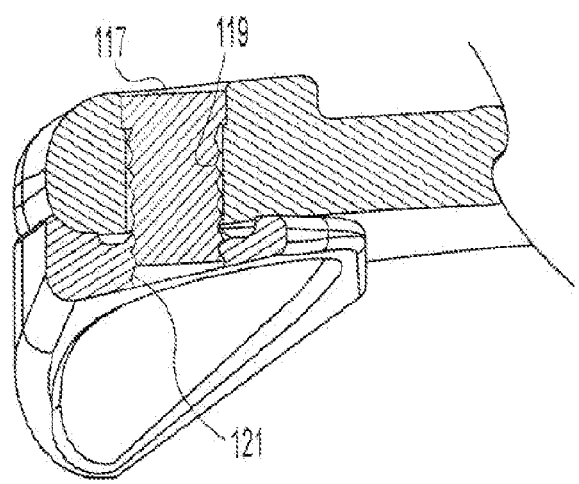

Alternatively for example referring to FIGS. 1 and 12 as discussed above it should be noted that connector 110, first connector portion 112 and second connector portion 114 may include many different structures configured to attach spacer segment 108 and plate 102. Referring to FIG. 11, a snap-fit type structure of connector 110 may include first connector portion 112 and second connector portion 114 having cooperating limiting walls 113 and 115. For example, limiting walls 113 and 115 may overlap upon an amount of insertion of extending, portions 160 and 162 into the opening defined by internal wall 144. As such, the elastic movement of extending portions 160 and 162 upon insertion into the opening, and the subsequent overlapping of limiting walls 113 and 115, may snap fit spacer segment 108 and plate 108. In another alternative, referring to FIG. 12, a screw type of connector 110 may be used to connect spacer segment 108 and plate 102. For example, connector 110 may include a screw member 117 having external threads 119 that cooperate, with internal thread 121 of spacer segment. As such, spacer segment 108 and plate 102 may be connected by inserting screw member 117 into an opening, through plate 102 so that external threads 119 can engage internal threads 121 within a corresponding opening in spacer segment 108. Optionally, plate 102 may include internal threads and the screw member 117 may be inserted through the spacer segment 108 and threaded into plate 102. Optionally, threads may be formed in both spacer segment 108 and plate 102.

Figure 13:
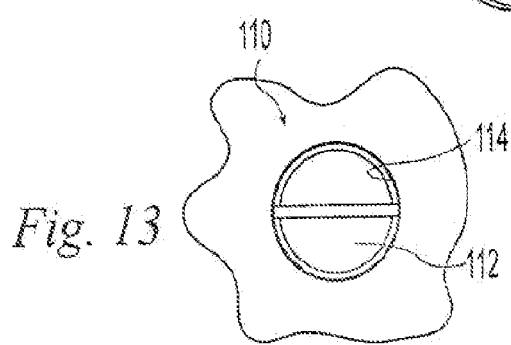
FIGS. 13 and 14 are partial top views of different aspects of a connector of FIG. 1, with FIG. 14 including anti-rotational surfaces.
Figure 14:
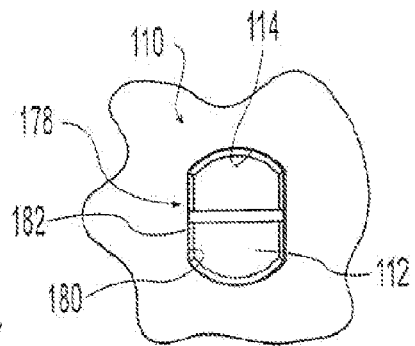
Figure 15:
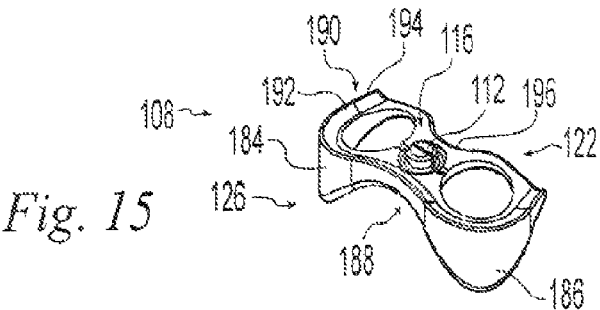
FIGS. 15-20 are a top perspective view, an end view, a top view, an opposing end view, a side view and a bottom view of an aspect of a spacer segment of FIG. 1.
Figure 16:
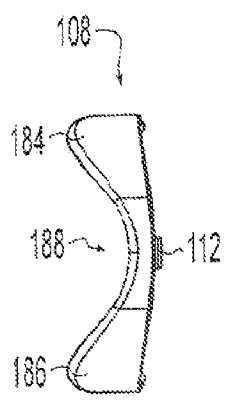
Figure 17:
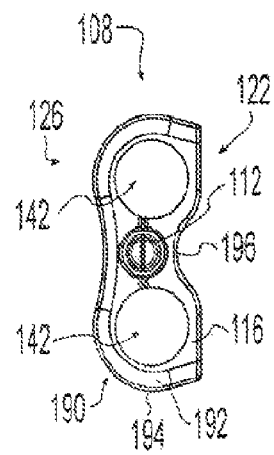
Figure 18:
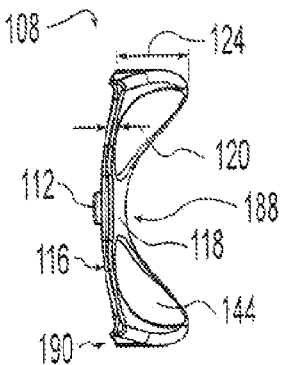
Figure 19:
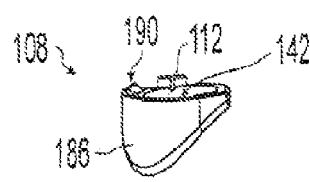
Figure 20:
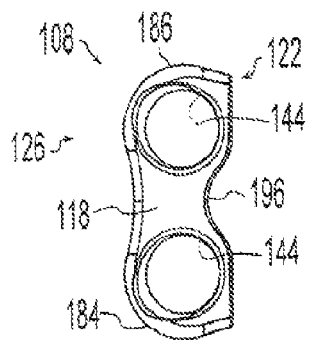
Figure 21:
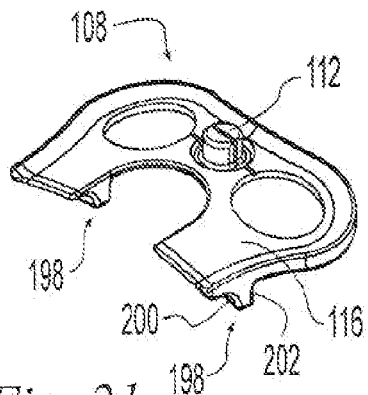
FIGS. 21-27 are a top perspective view, a bottom perspective view, a side view, a top view, an end view, a bottom view, and a sectional view along line 27-27 of FIG. 26, respectively, of an aspect of a spacer segment of FIG. 1.
Figure 22:
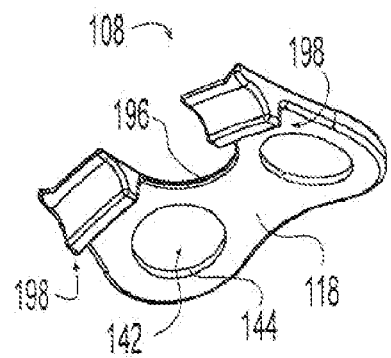
Figure 23:
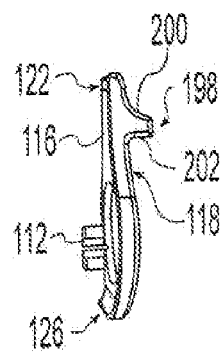
Figure 27:
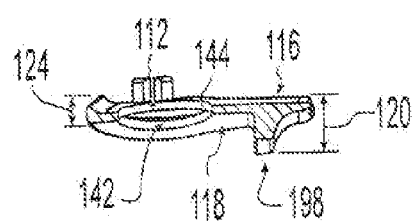
Figure 24:
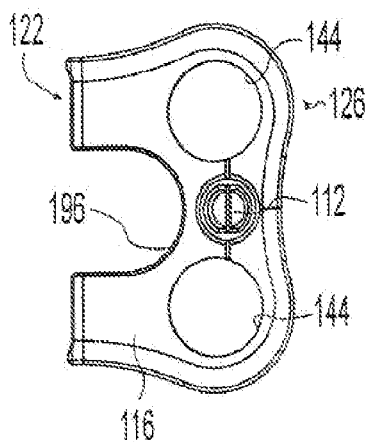
Figure 25:
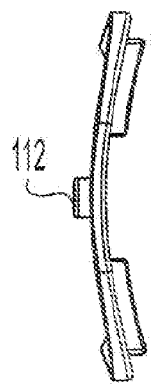
Figure 26:
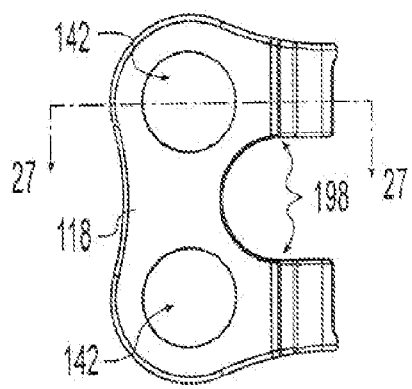
Figure 28:
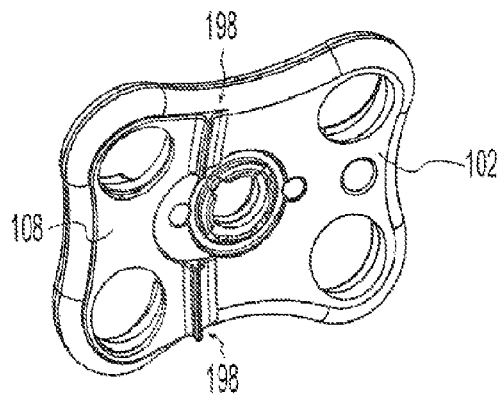
FIGS. 28-31 are a bottom perspective view, a side view, a bottom view and a sectional view along line 31-31 of FIG. 30, respectively, of an aspect of the plate and spacer segment described herein.
Figure 29:
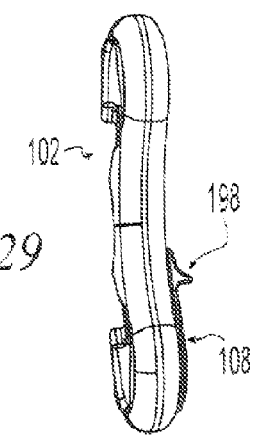
Figure 30:
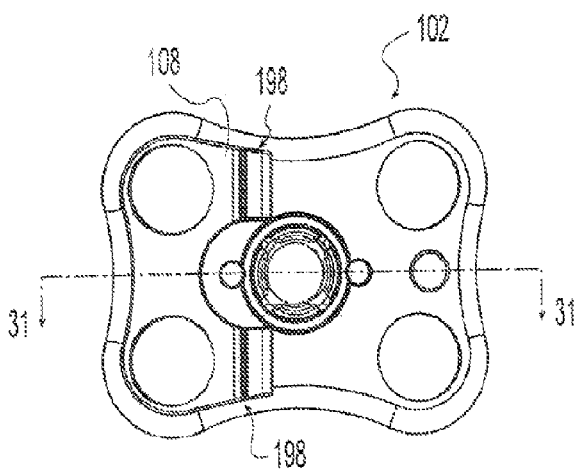
Figure 31:
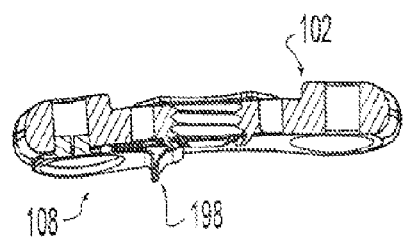
Figure 32:
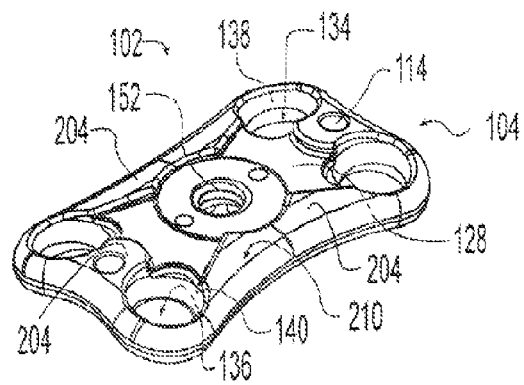
FIGS. 32-36 are a top perspective view, a top view, an end view, a side view, and a bottom view, respectively, of the plate of FIG. 1.
Figure 33:
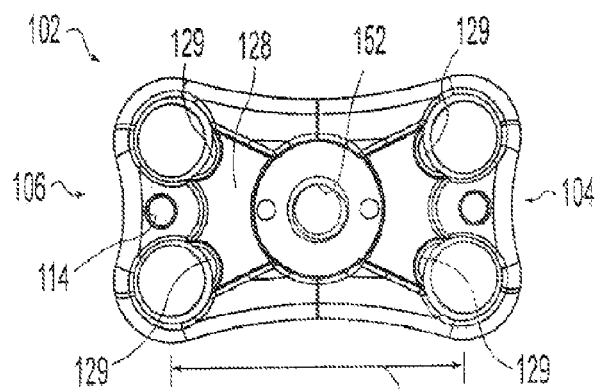
Figure 34:
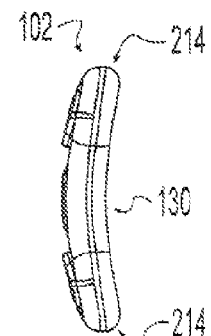
Figure 35:
Figure 36:
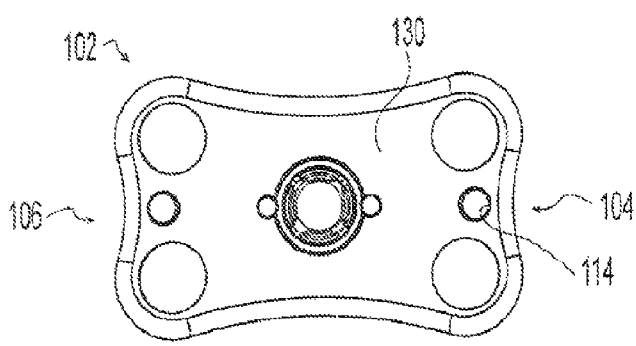

Also, for example referring to FIGS. 13 and 14, in an aspect (FIG. 13), connector 110 may be substantially circular, thereby potentially allowing relative rotation in at least one plane, e.g. a plane normal to the corresponding plate and spacer segment surfaces. Whereas, in another aspect (FIG. 14), connector 110 may additionally include at least one anti-rotation portion 178 configured to limit relative rotation in at least one plane between spacer segment 108 and plate 102. In an aspect, for example, anti-rotation portion 178 may include one or more corresponding flat surfaces 180 and 182 respectively formed on first connector portion 112 and second connector portion 114 which limit or substantially prevent relative rotation, such as in a plane between second plate surface 130 and first spacer surface 116. Anti-rotation portion 178 may include other structures that prevent relative rotation, such as a non-circular surface, a key, a spline, a plate-conforming surface, or any other corresponding surfaces on spacer segment 108 and plate 102 that interfere upon a given amount of relative rotation, in at least one plane, between spacer segment 108 and plate 102.

Additionally, with regard to connector 110, it should be understood that first connector portion 112 and second connector portion 114 may reversed, or, in other words, associated with an opposite one of spacer segment 108 or plate 102 as compared to the illustrated example.

Moreover, while one example of connector 110 has been described above in detail, it should be understood that connector 110 may comprise any mechanism that enables a connection between, or a disconnection of spacer segment 108 and plate 102. For example, connector 110 may include, but is not limited to any one or my combination of a force-fit connector, a screw mechanism, a keyed connector, a corresponding tenon and mortise, a splined connector, an adhesive, a dovetail connection, a sliding fit, a press fit, a keyed spline, a snap fit, or a screwed or threaded connection.

Referring to FIGS. 15-20, in an aspect of spacer segment 108, first spacer surface 116 and second spacer surface 118 may define a body of spacer segment 108 as a curved plate, which substantially corresponds to a curvature of plate 102. For example, in a lateral direction, the curvature may correspond to a corresponding curvature of a bone segment, such as a lateral curvature of a surface of a vertebra. Further, for example, in a longitudinal direction, the curvature may correspond to a corresponding curvature of adjacent hone segments, such as normal and/or abnormal spinal curvature, including kyphosis or lordosis.

Further, in the optional aspect when second spacer thickness 124 has a size greater than first spacer thickness 120, second spacer end 126 may have second spacer thickness 124 across all or only one or more portions of the end. For example, in an aspect, second spacer end 126 may include one or more protrusions, such as protrusions 184 and 186 positioned toward the respective corners of second spacer end 126. In use for spinal stabilization, for example, protrusions 184 and 186 have a curved body with a bone-facing surface shaped to correspond to a longitudinal and lateral curvature in a surface of an adjacent vertebra. In other words, protrusions 184 and 186 have a respective body and thickness 124 to substantially fill a gap between second plate surface 130 and the corresponding surface of the adjacent vertebra when plate 102 is placed in a stabilization position relative to the vertebra. As such, in some aspects, protrusions 184 and 186 may have a ramp-like or claw-like shape.

Further, in some aspects, first spacer end 122 may form a relatively narrow edge where first spacer surface 116 and second spacer surface 118 meet, thereby allowing first spacer end 122 to become substantially flush with second plate surface 130 when spacer segment 108 is connected to plate 102.

Additionally, in some aspects, spacer segment 108 may include a bridging surface 188 that may connect protrusions 184 and 186. Bridging surface 188 may conform to a shape of the adjacent bone segment, or have a lesser or greater radius of curvature than a typical lateral curvature of the adjacent bone segment, or have any shape that provides a space between bridging surface 188 and the surface of the bone segment. For example, such a space may be desired in order to allow tissue, muscle, or other anatomical features to be positioned between spacer segment 108 and the surface of the bone segment without the edge of spacer segment 108 compressing and/or cutting the anatomical features.

Additionally, in some aspects, spacer segment 108 may include a ridge 190 extending from first spacer surface 116 along at least a portion of a perimeter of spacer segment 108. For example, in some aspects, ridge 190 is formed along substantially all or along selected portions of the perimeter of spacer segment 108 that correspond to the perimeter of plate 102, e.g. along all or parts of the perimeter of spacer segment 108 except for first spacer end 122. Ridge 190 includes a ridge surface 192 that extends from first spacer surface 116 to a peak 194 of ridge 190. Ridge surface 192 may be a flat surface, a curved surface, or some combination of both. Further, in some aspects, additionally referring back to FIG. 6, ridge surface 192 matches or conforms to a shape of the corresponding second plate surface 130 and/or an edge of plate 102. Further, in some aspects (additionally see FIG. 6), ridge surface 192 may extend an amount such that peak 194 is positioned beyond, or ridge surface 192 overlaps with, second plate surface 130. As such, in these aspects (additionally see FIG. 6), ridge surface 192 may resist relative rotational movement in at least one plane between spacer segment 108 and plate 102 through contact with an edge of plate 102. Further, ridge surface 192 may be tapered so as to provide a low profile mating surface with edge of plate 102. Additionally, ridge surface 192 extends a thickness of spacer segment 108, thereby providing more material and allowing spacer segment 108 to be shaped to avoid or reduce sharp edges that can cut anatomy or cut a surgeon or nurse during a procedure.

Further, in some aspects, spacer segment 108 may additionally include to curved portion 196 at first spacer end 122 to reduce material cost or to provide clearance for structural features on the corresponding portion of second plate surface 130.

Referring to FIGS. 21-31, in other aspects, such as when first sparer thickness 120 is greater than second spacer thickness 124, spacer segment 108 may have at least one ledge portion 198 projecting from second spacer surface 118. In some aspects, such as in spinal applications, ledge portion 198 may also be referred to as a posterior shelf. In other words, an amount of protection of ledge portion 198 from second spacer surface 118 defines second spacer thickness 120 at at least a portion of second spacer end 122. In some aspects, ledge 198 may include opposing ledge surfaces 200 and 202 that are connected at an end to form ledge portion 198. For example, ledge surfaces 200 and 202 may be linear, curved, or curvilinear. Additionally, in some aspects, ledge surfaces 200 and 202 may have different curvatures. Also, in some aspects, one surface, such as surface 202 or the surface facing toward through-holes 142, may be substantially linear and positioned substantially normal to spacer second surface 118 and extend a sufficient amount so as to allow surface 202 to be positioned against an edge of a corresponding bone segment, such as against a superior or inferior edge of a vertebra. As such, in some aspects, ledge portion 198 allows plate 102 to be positioned or indexed relative to the adjacent bone segment, for example, to insure a relative position of bone screws in the adjacent bone segment. In other aspects, the positioning of ledge portion 198 against an adjacent bone segment provides support to plate 102, for example, thereby relieving force received by bone screws affixing plate 102 to the adjacent bone segment. Further, in an aspect where each end of plate 102 includes a respective spacer segment 108 with a respective ledge portion 198, the opposing ledge portions may assist in providing a desired spacing between adjacent bone segments, such as adjacent vertebrae.

Referring to FIGS. 32-36, in an aspect of plate 102, first plate surface 128 and second plate surface 130 may define a body of plate 102 as a curved plate. For example, in a lateral direction, the curvature may correspond to a corresponding curvature of a bone segment, such as a lateral curvature of a surface of a vertebra. Further, for example, in a longitudinal direction, the curvature may correspond to a corresponding curvature of adjacent bone segments, such as normal and/or abnormal spinal curvature, including kyphosis or lordosis.

In some aspects, additionally referring to FIG. 6, plate 102 includes a border portion 204 extending from first plate surface 128 along at least a portion of a perimeter of plate 102 between first plate end 104 and second plate end 106. As such, plate 102 comprises a first plate thickness 206 between first plate surface 128 and second plate surface 130 and a second plate thickness 208 at border portion 204, e.g. between first border surface 210 and second plate surface 130. In some aspects, second plate thickness 208 is greater than first plate thickness 206, thereby providing plate 102 with increased strength to resist bending as compared to a plate having only first plate thickness 206.

Figure 2:
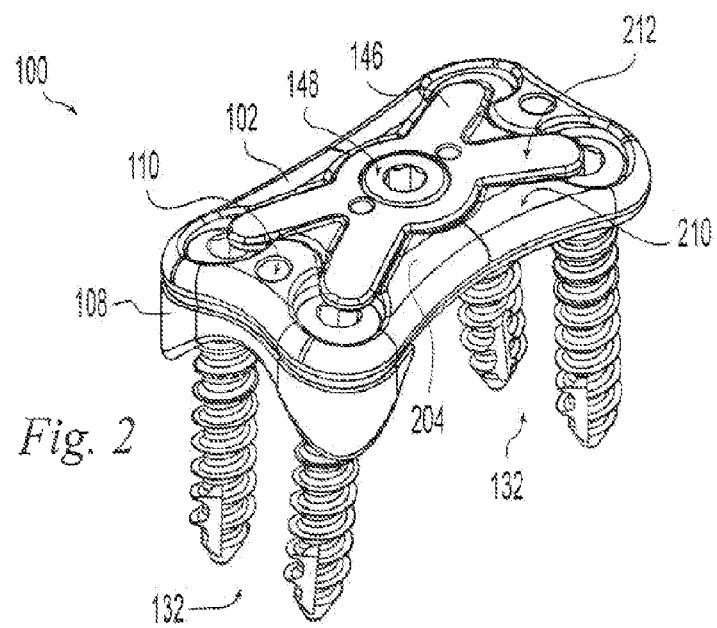
FIG. 2 is a perspective view of the bone plating system of FIG. 1.
Figure 3:
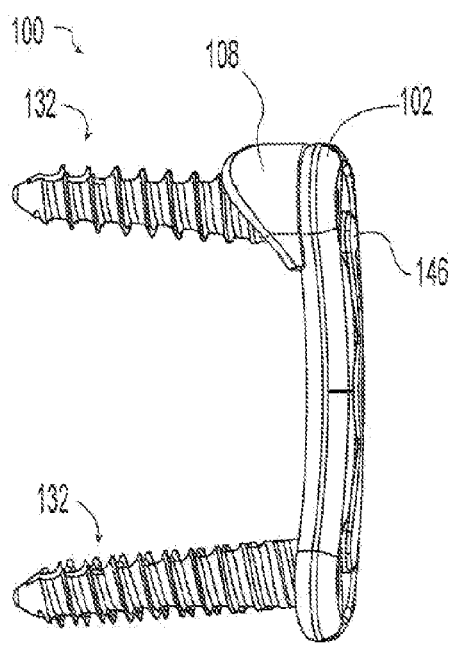
FIG. 3 is a side view of the bone plating system of FIG. 2.
Figure 4:
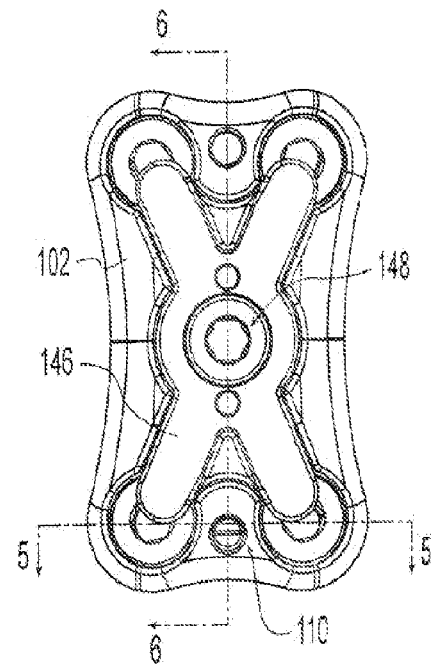
FIG. 4 is a top view of the bone plating system of FIG. 4.

Additionally referring to FIGS. 2 and 6, in some aspects, first border surface 210 may be configured to be substantially flush with first cover plate surface 212 when cover plate 146 is attached to plate 102. The relative flushness of the surfaces enables the assembled components to avoid catching, or snagging, anatomical structures.

In some aspects, border portion 204 has a greater area longitudinal cross sectional area in some portions of plate 102 than in other portions of plate 102. For example, border portion 204 may extend further laterally inward toward the center of the longitudinal length of plate 102 in order to provide greater resistance to bending in this area, which may experience higher bending forces than other portions of plate 102, such as plate ends 104 and 106. Additionally, in some aspects, border portion 204 may extend through portions of first plate end 104 and second plate end 106, such as between through-holes 134 and 136. As such, border portions 204 at plate ends 104 and 106 may provide additional rigidity to connector 110 or connector portion 114, as well as increased surface area on internal walls 138 and 140 against which a head portion of each securing mechanism 132 may bear and/or slidingly engage to allow for at least partial rotation of one or more securing mechanisms 132. It should be noted that border portions 204 may be formed on plate 102 to enable plate 102 to have a desired stiffness. In other words, border portions 204 may be configured into any desired size, shape or thickness to achieve a desired stiffness. For example, plate 102 or the combination of the components of plating system 100 may be designed to have any desired stiffness, such as a stiffness comparable to a stiffness of the adjacent bone to which plating system 100 is attached, or a greater stiffness, or a lesser stiffness, which may be controlled in part by the configuration of border portions 204.

Additionally, plate 102 includes a side edge 214 that connects first plate surface 128 and second plate surface 130. Side edge 214 may be linear, curved, or curvilinear. Additionally, as discussed above with regard to aspects of spacer segment 108, at least a portion of side edge 214 and an adjacent portion of second plate surface 130 may have a shape that substantially matches a shape of ridge 190 on spacer segment 108.

Further, in some aspects, such as in spinal applications, plate 102 may be additionally configured such that through-holes 134 and 136 are spaced apart a sufficient distance 216 to allow plate 102 to be affixed to the two adjacent vertebrae, such that plate 102 spans the corresponding disc space.

Additionally, in some aspects, referring to FIGS. 33 and 37-43, plate 102 may further include respective shelf portions 129 to make room for, or support, corresponding pad structures 131 that extend from a bottom surface 155 of cover plate 146. As such, shelf portions 129 enable rover plate 146 to be mounted relatively flush with a highest portion of plate 102, enable the assembly to maintain a low profile. Further, for example, pad structures 131 provide additional thickness to cover plate 146, which enables the edges of rover plate 146 to be rounded to avoid having thin, sharp edges that may cut anatomy or a person involved in a surgical procedure. Correspondingly, shelf portions 129 each define a relief, or surface portions positioned closer to bottom or second plate surface 130, on top or first plate surface 128 sized to accommodate or support pad structures 131. In other words, shelf portions 129 are inset from other parts of top or first plate surface 128 to allow cover plate 146 to be positioned relatively flush with a highest surface of plate 102, enabling plate 102 to maintain a low profile while still allowing edges of cover plate 146 have sufficient material to be rounded and avoid having sharp edges.

Figure 37:
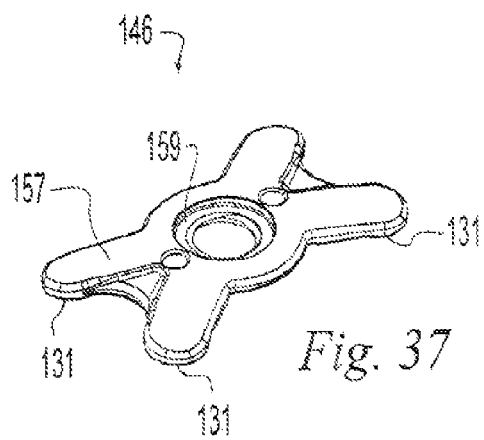
FIGS. 37-41 are a top perspective view, an end view, a side view, a bottom view and a bottom perspective view, respectively, of the cover plate of FIG. 1.
Figure 38:
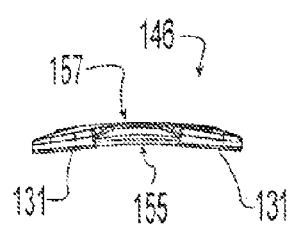
Figure 39:
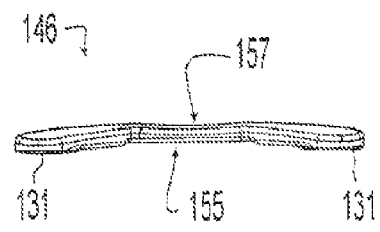
Figure 40:
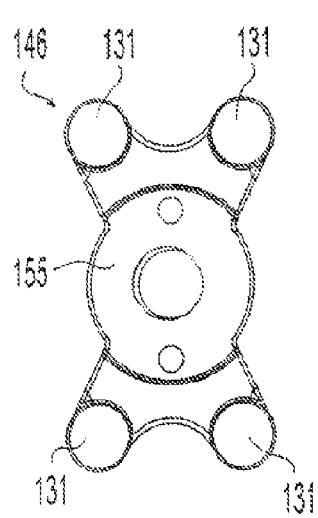
Figure 41:
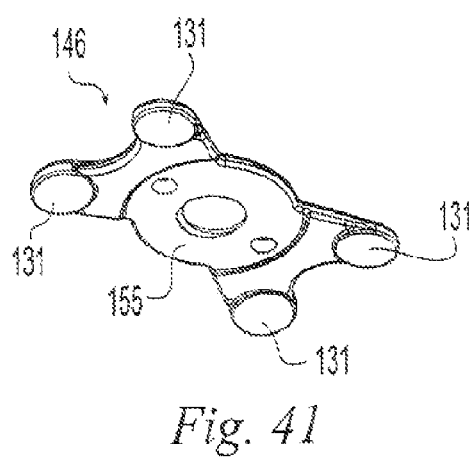
Figure 42:
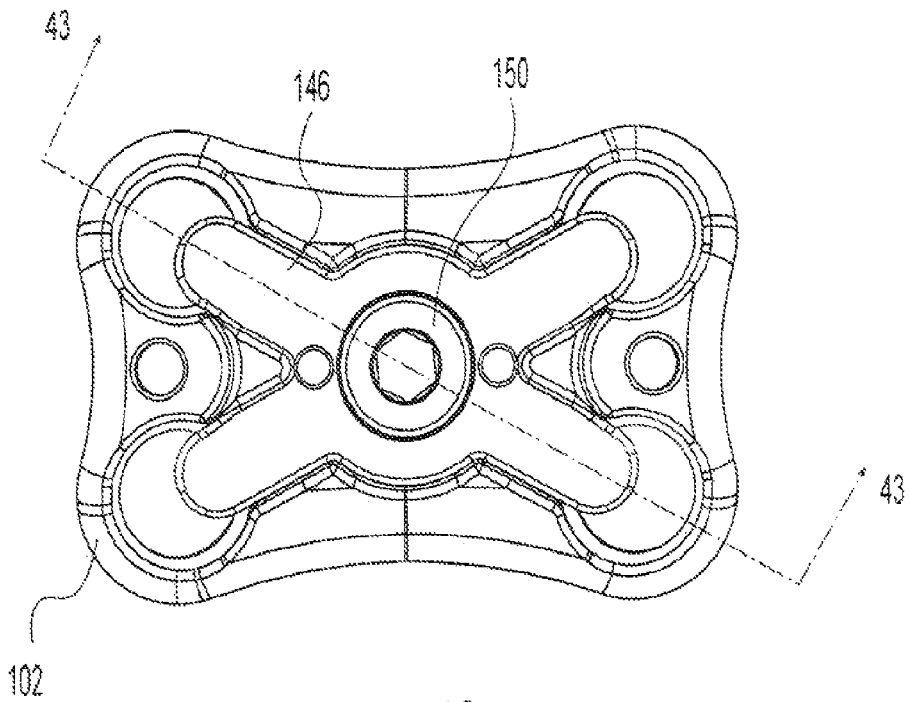
FIG. 42 is a top view of an aspect of the bone plating system of FIG. 1 with the hone fasteners omitted.
Figure 43:
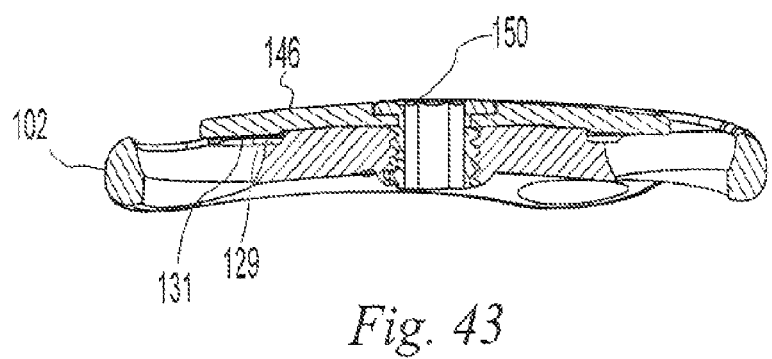
Figure 44:
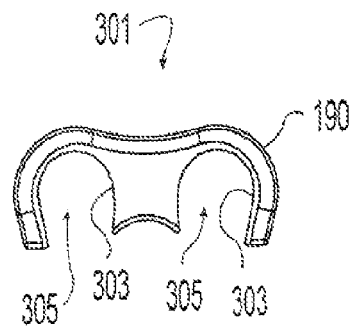
FIGS. 44-48 are top views of respective aspects of the spacer segment of FIG. 1.

Additionally, referring to FIGS. 1 and 37, cover plate 146 further includes a top surface 157 having a screw head relief surface 159 adjacent to the opening that receives first securing portion 150, such as a screw. Screw head relief surface 159 provides sufficient space to receive a flange or head portion of first securing portion 150, enabling a top surface of first securing portion 150 to be positioned substantially flush with, or below, top surface 157 of cover plate 146 upon assembly. For example, screw head relief surface 159 is positioned below top surface 157 of cover plate 146, closer to bottom surface 155 of cover plate 146 than adjacent portions of top surface 157. As such, screw head relief surface 159 allows first securing portion 150 to maintain a low profile with respect to cover plate 146 upon connecting cover plate 146 to plate 102.

Referring to FIGS. 44-51, spacer segment 108 may include any number of variations. For example, retelling to FIG. 44, spacer segment 301 may include wall 303 defining respective openings 305 sized to receive securing mechanisms 132 (FIG. 1), but not completely encompassing securing mechanisms 132. For example, in an aspect, open end of openings 305 may have a size greater than a corresponding size of securing mechanisms 132 such that securing mechanisms 132 do not capture spacer segment 301. Further, in another optional aspect, referring to FIG. 44, spacer segment 301 may not include connector 110 (FIG. 1) or connector portion 112 (FIG. 1), but instead may utilize ridge 190 (also see FIGS. 15-20) to mate with a sufficient amount of an edge of plate 102 (FIG. 1) to prevent relative movement between spacer segment 301 and plate 102, in at least one plane, when plate 102 is fixed to an adjacent bone segment. For example, the sufficient amount of the edge of plate 102 for engagement with ridge 190 may include a continuous section, or discrete points, and the at least one plane may include a plane corresponding to the interface between a top surface of spacer segment 301 and a bottom surface of plate 102.

Figure 45:
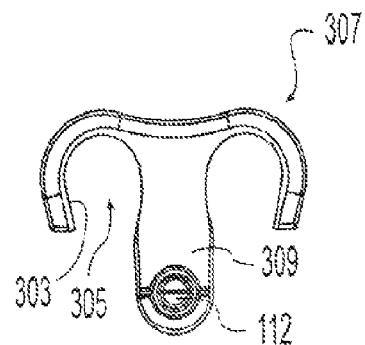

In another optional aspect, referring to FIG. 45, spacer segment 307 may include connector 110 (FIG. 1) or first connector portion 112 positioned on a flange member 309 to enable the corresponding second connector portion 114 (FIG. 1) to be positioned out of alignment with through-holes 136 in plate 102. As such, changing the positioning of second connector portion 114 (FIG. 1), which may be a through hole, with through-holes 136, allows plate 102 to be configured to have different strengths or stiffnesses in regions adjacent to the holes. Additionally, in some aspects, spacer segment 307 may include openings 305, as discussed above in FIG. 44, and also include first connector portion 112 to insure improved connection between plate 102 and spacer segment 307.

Figure 46:
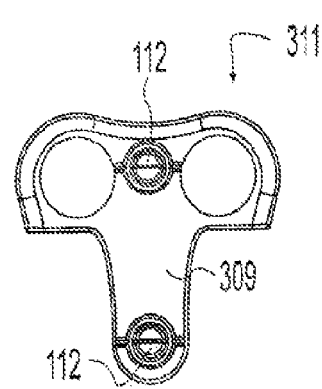

In another optional aspect referring to FIG. 46, spacer segment 311 may include at least two first connector portions 112, each mating with a corresponding second connector portion 114 (as in FIG. 1), to provide two points of connection that resist relative rotation between spacer segment 311 and plate 102 (FIG. 1). For example, in an optional aspect, one of the two first connector portions 112 may be positioned on flange member 309.

Figure 47:
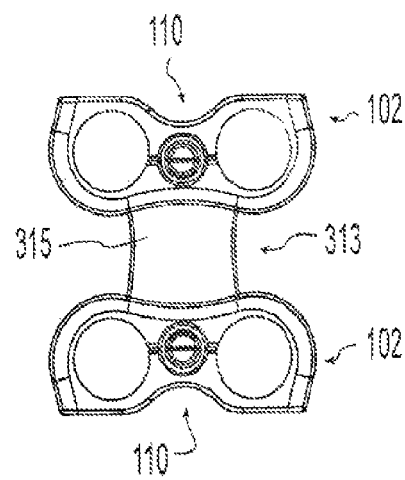

In another optional aspect, referring to FIG. 47, a spacer segment 313 may connect two different plates 102, such as via two connectors 110 spaced apart across an extension member 315. For example, in a spinal application, if a procedure calls for stabilization over two levels, e.g. across two disc spaces spanning three adjacent vertebrae, and if only single level plates are available, then spacer segment 313 may be utilized to securely connect two plates 102 across the two levels.

Figure 48:
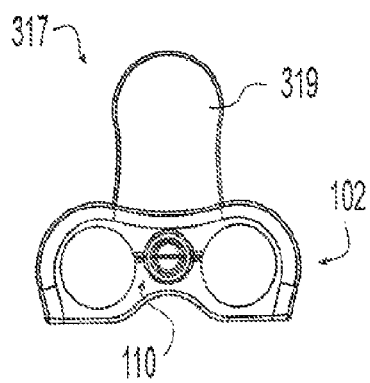

Referring to FIG. 48, in another optional aspect, a spacer segment 317 may include a buttress 319 extending from spacer segment 317 in a direction away from plate 102. For example, in a spinal application, buttress 319 may have a size and/or shape sufficient to extend across at least a portion of an adjacent disc space to hold in, or block expulsion of, an implant positioned within the adjacent disc space.

Figure 49:
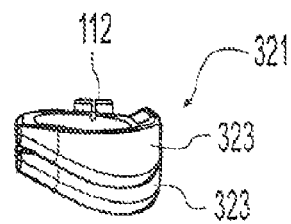
FIG. 49 is a side view of an aspect of the spacer segment of FIG. 1.
Figure 50:
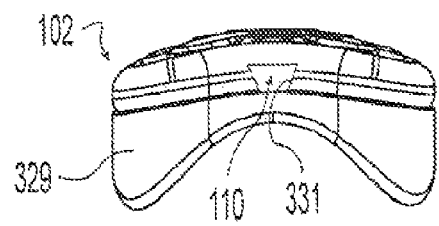
FIG. 50 is an end view of an aspect of the spacer segment of FIG. 1.

Referring to FIG. 49, in an optional aspect, a spacer segment assembly may include more than one spacer segment. For example, spacer segment assembly 321 includes to of a same type of spacer segment 323 in order to form an assembly hang a larger size and different shape as compared to a single spacer segment 323. Further, for example, spacer segment assembly 321 may hie hide two different types of spacer segments, e.g. such as a claw-shaped spacer segment and a buttes spacer segment or a ledge defining spacer segment and a claw shaped spacer segment or a thick and a thin spacer segment or any other desirable combination. Referring to FIG. 50, in an optional aspect, connector 110 that secures spacer segment 329 to plate 102 includes a dovetail or key structure 331 that enables a connection to be made via a sliding motion in a direction or plane substantially parallel to a longitudinal length of plate 102. It should be understood, however, that dovetail or key structure 331 may be configured so that the sliding motion may be in any direction substantially parallel to a plane of plate 102. Further, with dovetail or key structure 331, the respective spacer segment or segments and plate 102 can be further secured together by a snap-fit, press-fit or detent formed in one of the spacer segment or the plate, or by securing mechanisms such as bone screws extending through the plate and spacer segment(s).

Figure 51:
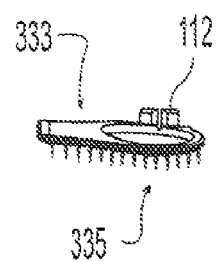
FIG. 51 is a side view of an aspect of the spacer segment of FIG. 1.

In another optional aspect, referring to FIG. 51, a spacer segment 333 may include a surface element 335 modifying the engagement with a surface of an adjacent bone segment. For example, surface element 335 may include a coating, roughened texture, spikes, pores or bone in-growth openings, smooth surface or any other structure or mineral to modify the engagement with a surface of an adjacent bone segment. In some aspects, surface element 335 may change the properties of the bottom surface of spacer segment 133 without substantially changing a size and/or shape of spacer segment 333. In some aspects, surface element 335 may increase adherence of spacer segment 333 to an adjacent bone segment. In some aspects, surface element 335 may decrease adherence of spacer segment 333 to an adjacent bone segment. Different spacer segments 333 having different surface elements 335 may be provided to allow the use to customize the spacer segment 333 interface with the adjacent bone segment according to the user's preference.

Figure 52:
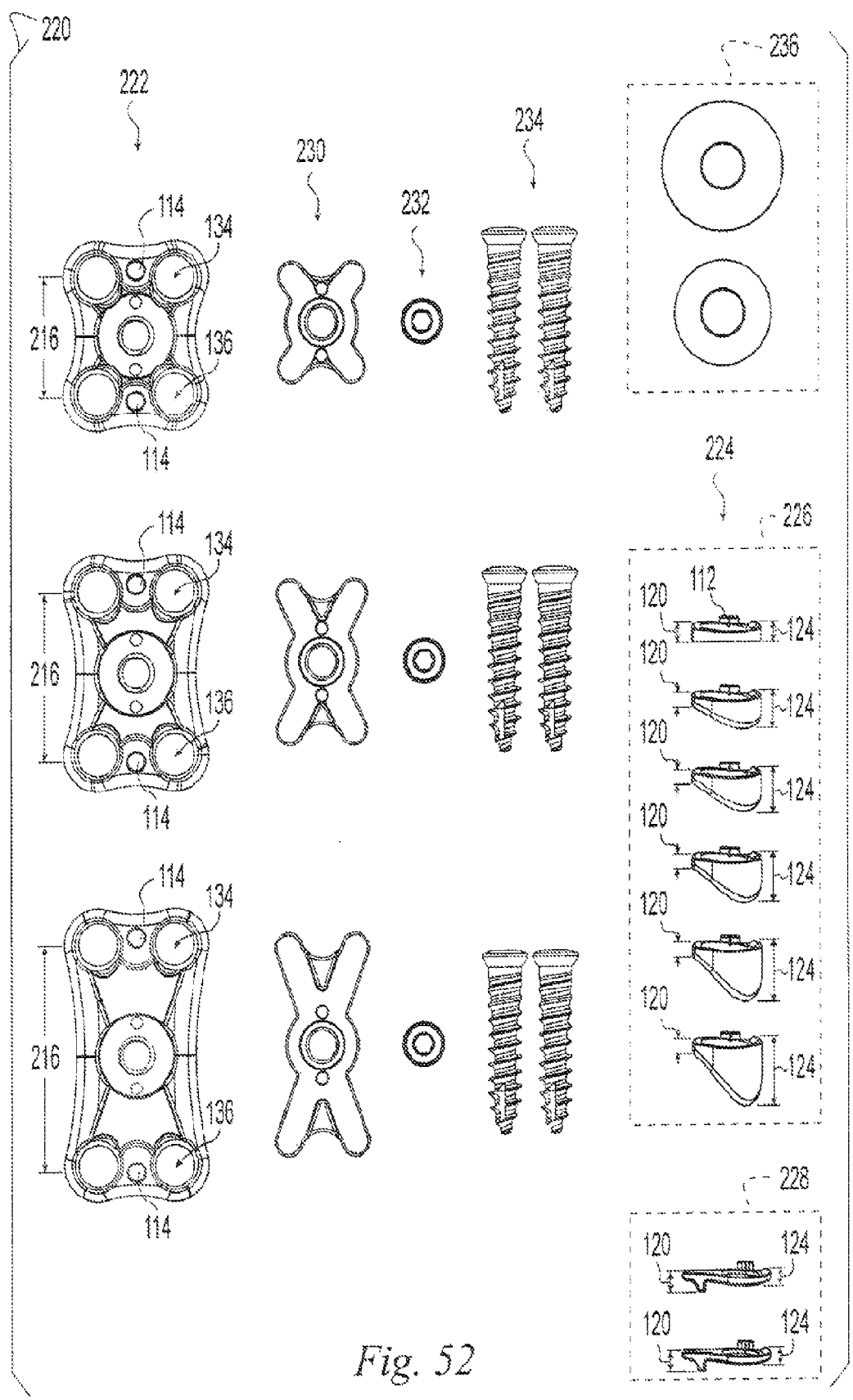
FIG. 52 is a diagram of an aspect of a bone plating set including the plate and spacer segment of FIG. 1.

Referring to FIG. 52, in another aspect, such as for a surgical application, system 100 may include a bone plating set 220 that includes a plurality of plates 222 interchangeably connectable with a plurality of spacer segments 224 such that a selected one of the plates 222 and a selected one of the spacer segments 224 may be matched to the respective anatomy of a patient. For example, each of the plurality of plates 222 may be substantially similar to plate 102 (FIG. 1), but the plurality 222 may include plates having different longitudinal lengths, or in spinal applications the plurality 222 may include plates able to span multiple vertebral levels. In other words, the plurality of plates 222 may include one or more plates of different longitudinal lengths, or having a different distance 216 between through-holes 134 and 136, or having different numbers of pairs of through-holes. Also for example, each of the plurality of spacer segments 224 may be substantially similar to spacer segments described herein 1, 15, 21, or 44-51), but the plurality 224 may include spacer segments having different shapes and/or different sizes. The plurality 224 may have different sets 226, 228 having different characteristics, e.g. including any combination of the plurality of spacer segments described herein. For example, the plurality of spacer segments 224 may include a first sets of one or more spacers 226 with the same or with different thicknesses 124 at one end compared to thicknesses 120 at an opposite end, or a second set of one or more spacers 228 with the same or with different thicknesses 120 at one end (opposite end with thickness 124 of first set 226), or different shapes as shown in FIGS. 1, 15, 21, 44-51, or any combination thereof. For example, the first set 226 and the second set 228 of spacers may include duplicates of the same configuration, for instance, to allow for two spacers of the same configuration to be used on different ends of the same plate. For example, in the hone plating set of FIG. 52, the first set 225 includes mismatch filling spacer segments having varying thicknesses 124 at one end and a constant thickness 120 at an opposite end such that the set 226 presents a range to the user of from thickness 124 equal to thickness 120 to thickness 124 being several times thicker than thickness 120 and second set 228 includes relatively thin spacers having a ledge portion 198 useful, for example, for indexing the spacer segment to an edge of a bone segment.

Additionally, in some optional aspects, each of the plurality of plates 222 and the plurality of spacer segments 224 may further include corresponding connector portions 112 and 114 to define connector 110, where connector portions 112 and 114 are substantially similar so as to allow each of the plates and each of the spacer segments to be used interchangeably.

In other words, set 220 comprises a bone plating set having component parts capable of being assembled in an operating environment for providing stabilization between adjacent bone segments, where the set comprises a combination of plates and spacer segments that can be mixed and matched to form a plating system that conforms to the anatomy of the adjacent bone segment or segments. Further, in some aspects, each spacer segment further comprises a first spacer thickness at a portion of the first spacer end and a second spacer thickness at a portion of the second spacer end, wherein the second spacer thickness is greater than the first spacer thickness, and wherein each of the plurality of spacer segments is adapted to be removably secured to each plate one or both plate ends.

Optionally, bone plating set 220 may further include a plurality of cover plates 230, wherein the plurality 233 includes different sized cover plates to correspond to the different sized one of the plurality of plates 222. For example, each of the plurality of cover plates 230 may be substantially similar to cover plate 146.

Optionally, bone plating set 220 may further include a plurality of cover securing mechanisms 232, wherein each of the covering securing mechanisms substantially corresponds to securing mechanism 148 (FIG. 1), e.g. is a screw type mechanism.

Optionally, bone plating set 220 may further include a plurality of plate securing mechanisms 234, wherein each of the plate securing mechanisms substantially corresponds to securing mechanism 132 (FIG. 1), e.g. is a screw type mechanism, such as a bone screw.

Optionally, bone plating set 220 may further include a plurality of buttress washers 236, which may be used in combination with one of securing mechanisms 234 to provide an interfering surface to prevent displacement of an implant, such as a fusion implant positioned between adjacent vertebrae stabilized by the plate.

Figure 53:
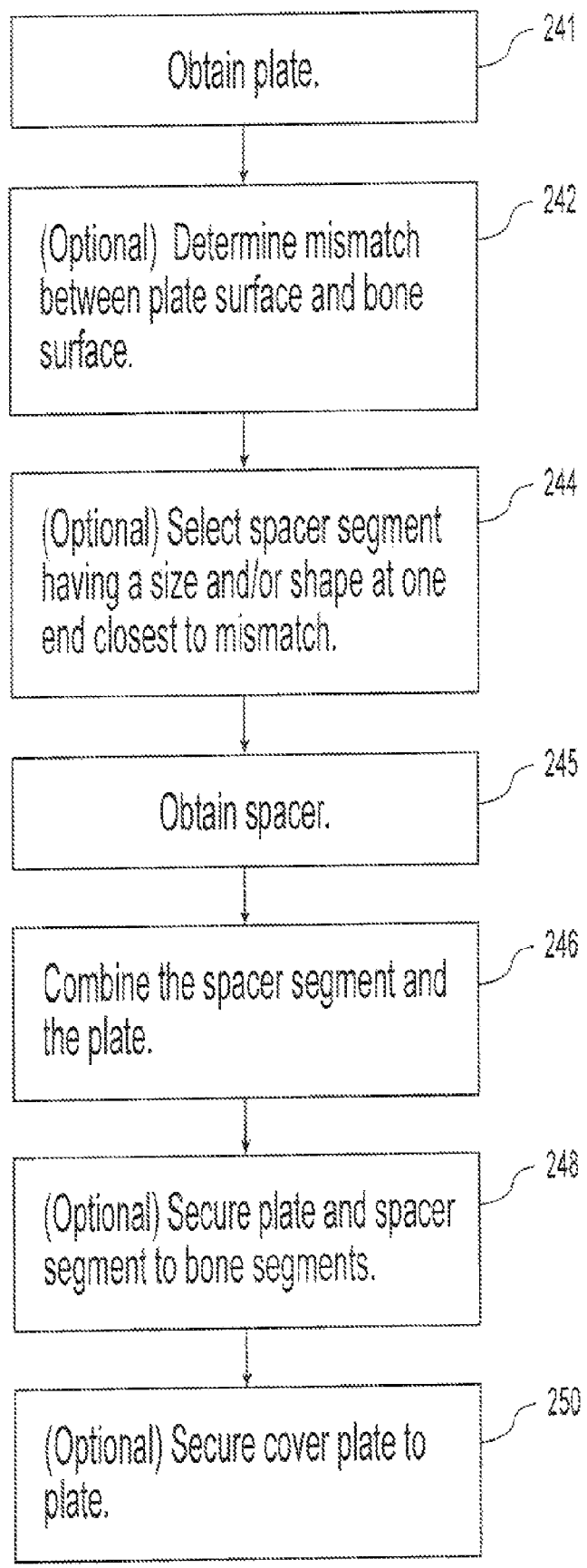
FIG. 53 is a flowchart of an aspect of a method of bone stabilization.

Referring to FIG. 53, in operation, the described plate 102 and spacer segment 108 may be utilized in a method 240 of fixating bone segments. In an aspect, method 240 of fixating bone may include obtaining a plate (Block 241), and obtaining a spacer segment shaped to adapt the plate to conform to an adjacent bone segment surface (Block 245). For example, in an aspect, there may be a mismatch or a space between the bottom of plate and the facing surface of an adjacent bone segment. In this case, spacer segment may have a size or shape similar to at least a part of the mismatch or space. In another aspect, it may be desired to locate plate at a desired position relative to an adjacent bone segment, and spacer segment may include a structure, such as a ledge or shelf, that aids in indexing or positioning plate relative to the adjacent bone segment. Additionally, method 240 may further include combining the plate and the spacer segment (Block 246). For example, plate and spacer segment are combined for placement on and affixing to an adjacent bone segment.

Optionally, method 240 may further include securing one end of the plate and the selected spacer segment to a first bone segment, and securing an opposite end of the plate to an adjacent second bone segment (Block 248). For example, the plate may be positioned to span fractured or spaced apart bone segments, and bone screws may partially pass through the plate at one end, and the plate, and spacer segment at the other end, to affix the assembly to the bone segments.

Optionally, the method may also include securing a cover plate to the plate (Block 250). For example, in an aspect, after the plate and spacer segment have been attached to the bone segments, then a cover plate may be attached to the plate in a position to prevent or resist back-out of bone screws used to attach the plate and spacer segment to the adjacent bones.

In another aspect, method 240 may additionally include other actions, such as determining a size of a gap or mismatch between a surface of a plate and a surface of an adjacent bone (Block 242). For example, given a plate that longitudinally extends between a first plate end and a second plate end, and wherein the plate further comprises a first plate surface spaced apart from an opposing second plate surface, the gap may be defined between the second plate surface and the surface of the bone segment upon placing second plate surface against bone segment surface in a position where plate is desired to be affixed. In an aspect, for example, the gap may be determined upon placing second plate surface against bone segment surface in a position where plate is desired to be affixed and then using one or more of diagnostic imaging, such as using x-rays in a fluoroscopy, a mechanical measuring instrument, or trial-and-error (e.g. connecting and disconnecting spacer segments having different thicknesses) until a match with gap is found. Optionally, a measuring tool, template, or provisional or temporary implant may be used alone to gauge the required plate and spacer segment combination required to produce the desired fit on the bone.

Further, in the other optional aspect, method 240 may include selecting one of a plurality of spacer segments having a spacer thickness at one end sized closest to the size of the gap or shape of the underlying bone (Block 244). For example, the selected spacer segment may be chosen from a bone plating set having a plurality of spacer segments each longitudinally extending between a first spacer end and a respective second spacer end, wherein each spacer segment further comprises a first spacer surface spaced apart from an opposing second spacer surface defining a first spacer thickness at the first spacer end and the second spacer thickness at a portion of the second spacer end, wherein the second spacer thickness is greater than the first spacer thickness, and wherein each of the plurality of spacer segments has a different second spacer thickness.

Additionally, in the other optional aspect, with regard to combining the plate and the spacer segment (Block 246), method 240 may more specifically include removably fixing the selected one of the plurality of spacer segments to the plate. For example, the selected spacer segment and the plate may have corresponding connector portions 112 and 114 that define a connector 110 configured to removably affix the spacer segment and the plate. Further, for example, the connecter 110 may be universal such that each of the plurality of spacer segments is connectable with the plate.

Referring to FIGS. 54-59, different configurations of plate 102 and one or more spacer segments 108 are combined to stabilize or fixate adjacent bone segments 260 and 262. In some aspects, bone segments 260 and 262 may be positioned to abut against one another in order to promote osteosynthesis between the segments. In other aspects bone segments 260 and 262 may be spaced apart from one another by another structure 264, for instance, an anatomical structure such as a vertebral disc between adjacent vertebrae, or an implant such as a bone graft or fusion cage configured to enable fusion between the adjacent bone segments 260 and 262. Further, a bone growth promoting material 266 may be placed between adjacent bone segments 260 and 262, or included with structure 264, in order to promote osteosynthesis. Structure 264 and/or hone growth promoting material 266 may also be placed to facilitate fusion of adjacent vertebrae between spinous processes, laminae, transverse processes, facets, and/or other spinal structures. The bone growth promoting material may be spaced from the structure 264, placed adjacent the structure 264, sandwiched between the structure 264 and underlying bone, placed inside the structure 264, coated onto the structure 264, and/or otherwise placed relative to the structure 264 or independently without structure 264.

As used herein, bone growth promoting material may include hone paste, bone chips, bone strips, structural boric grafts, platelet derived growth factors, bone marrow aspirate, stem cells, bone growth proteins, hone growth peptides, bone attachment proteins, hone attachment peptides, hydroxylapatite, calcium phosphate, and/or any other material operable to induce or conduct one growth and fusion between adjacent bone segments 260 an 262.

Figure 54:
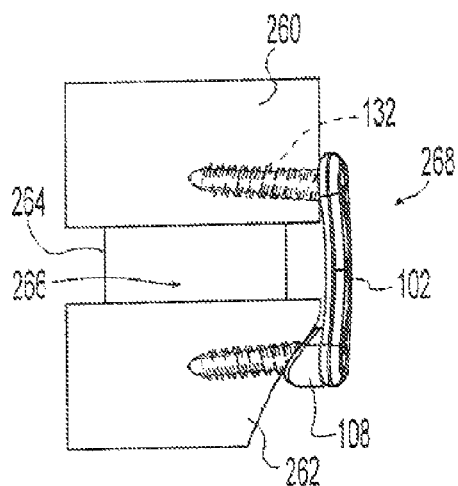
FIGS. 54-59 are side views of different aspects of the hone plate and spacer segment of FIG. 1.

More specifically, referring to FIG. 54, in an aspect, implant 268 includes plate 102 and spacer segment 108 having a greater thickness at one end, such as in the shape of a ramp or claw, to account for a displacement between bone segments 260 and 262, or to account for a sloping of one surface of hone segment 262 relative to an edge of the bone segment. In this case, the thicker end of spacer segment 108 is aligned toward the inferior end of plate 102. For instance, implant 268 may be utilized in a spinal procedure to stabilize the L5-S1 vertebrae.

Figure 55:
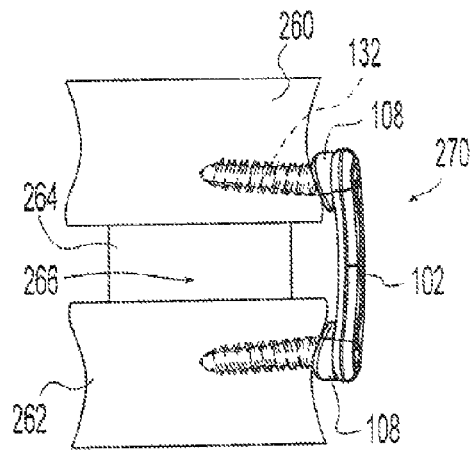

Referring to FIG. 55, in an aspect, implant 270 includes plate 102 and spacer segment 108 at both ends, such as may be utilized in a spinal procedure to stabilize adjacent bone segments 260 and 262, namely vertebrae, having concave surfaces adjacent to the ends of plate 102.

Figure 56:
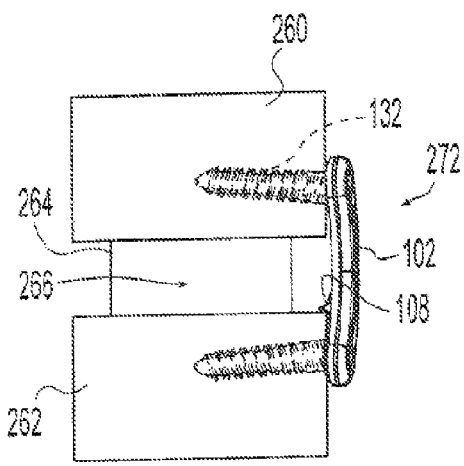

Referring to FIG. 56, implant 272 includes plate 102 and spacer segment 108 with a greater thickness at one end, for instance, forming a ledge, in this case, thr instance in a spinal procedure, the ledge may be positioned against a superior edge of bone segment 262, so as to stabilize adjacent bone segments 260 and 262, such as vertebrae, and/or provide for indexing the plate 102 and spacer segment 108 relative to bone segment 262 and/or to reduce load on inferior bone screws that affix plate 102 to bone segment 262.

Figure 57:
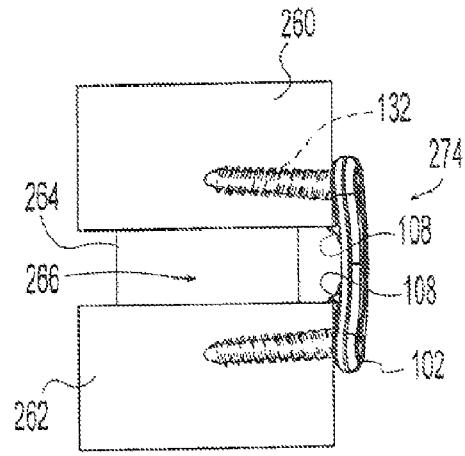

Referring to FIG. 57, in an aspect, implant 274 includes plate 102 and spacer segments 108 at both ends of plate 102, with each spacer segment having a greater thickness in the form of a ledge toward the center of plate 102. In this case, for instance in a spinal procedure, the respective ledges may be positioned against opposing edges of adjacent bone segments 260 and 262, namely vertebrae, so as to stabilize adjacent bone segments 260 and 262 and/or provide a desired spacing between adjacent bone segments 260 and 262 and/or reduce a load on bone screws used to affix plate 102 to bone segments 260 and 262, e.g. referred to as load sharing.

Figure 58:
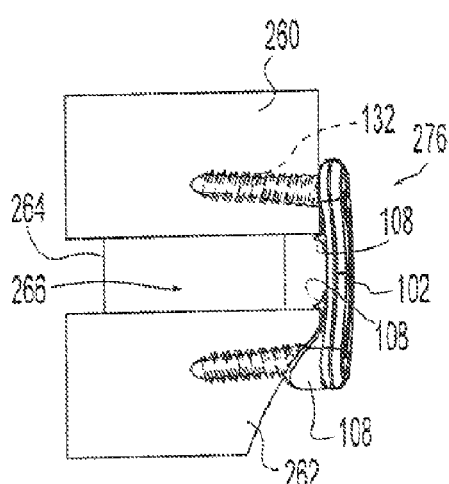

Referring to FIG. 58, in an aspect, implant 276 includes spacer segments 108 at both ends with two spacer segments stacked together at the inferior end. The spacer segments 108 are different sizes and shapes. For example, one spacer segment 108 may have a ledge toward the center of plate 102, while the other spacer segment 108 may have a ramp or claw-like portion toward an end of plate 102. Implant 276 may be utilized, for instance, in a spinal surgery application where the ledges assist in maintaining a spacing between adjacent bone segments 260 and 262, namely vertebrae, while the ramp accounts for a gap between the bottom of plate 102 and the facing surface of inferior bone segment 262, which may be displaced from or sloping away from the point where the plate 102 and bone segment 262 meet.

Figure 59:
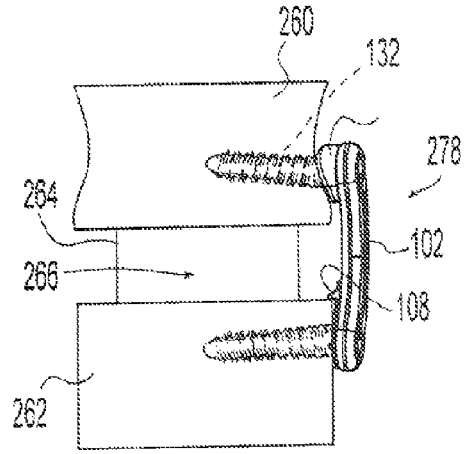

Referring to FIG. 59, in an aspect, implant 278 includes spacer segments 108 at both ends, with each spacer segment 108 having a different shape and size. For example, one spacer segment 108 may have a ramp or claw-like portion toward an end of plate 102, while the other spacer segment 108 may have a ledge toward the center of plate 102. Implant 278 may be utilized, for instance, in a spinal surgery application where the ramp accounts for a gap between the bottom of plate 102 and the facing surface of a superior bone segment 260, which may displaced from or sloping away from the point where the plate 102 and bone segment 260 meet, while the ledge assists in indexing the plate 102 and spacer segment 108 relative to bone segment 262 and/or to reduce load on inferior bone screws that affix plate 102 to hone segment 262.

It should be understood that FIGS. 54-59 are non-limiting examples of the potential applications of the aspects of bone plating system 100 described herein. The plate may be used alone and any of the spacer segments disclosed herein may be substituted for those shown in FIGS. 54-59 as desired to meet the needs of a particular patient.

Further, it is contemplated that plate 102 and spacer segment 108, or the assembled combination that forms an implant, may be constructed out of a number of different materials, such as, for example, bone, biocompatible metals, plastics, ceramics, and other synthetics, which may or may not be resorbable.

While the foregoing disclosure discusses illustrative aspects and/or embodiments, it should be noted that various changes and modifications could be made herein without departing from the scope of the described aspects and/or embodiments as defined by the appended claims. For example, with regard to spinal applications, although the described aspects relate to a plate or plating system configured to span a single vertebral level, e.g. a single disc space between two adjacent vertebrae, these aspects are intended to include a plate or plating system able to span multiple vertebral levels, in a multiple vertebral level aspect, the length of the plate may be extended to span the greater distance (relative to a single vertebral level) to one or more additional vertebrae, covering one or more additional disc spaces or levels. Further, additional through-holes may be included in the plate such that bone screws may affix the plate to any additional vertebral bodies adjacent to the plate. In other aspects, the plate may include one or more additional through-holes to enable bone screws to attach the plate to an implant, such as an intervertebral implant. Furthermore, although elements of the described aspects and/or embodiments may be described or claimed in the singular, the plural is contemplated unless limitation to the singular is explicitly stated. Additionally, all or a portion of any aspect and or embodiment may be utilized with all or a portion of any other aspect and/or embodiment, unless stated otherwise.

What is claimed is:

1. An apparatus adapted to facilitate a fusion between at least two boney segments, the apparatus comprising:
a plate longitudinally extending between a first plate end and a second plate end comprising an upper plate surface spaced apart from an opposing lower plate surface, the plate comprising at least one through hole in the first plate end and at least one through hole in the second plate end;
a plurality of fasteners adapted to extend through the through holes and removably couple the plate to the at least two boney segments; and
a first spacer segment removably coupled to the second plate end, the first spacer segment having a first spacer end, an opposed second spacer end that is closer than the first spacer end to the second plate end, and an uppermost surface extending from the first spacer end to the second spacer end, the second spacer end having a first corner, a second corner, and a medial portion extending from the first corner to the second corner, the first corner including a first through hole and a first extension extending downwardly from the uppermost surface, the second corner including a second through hole and a second extension extending downwardly from the uppermost surface, the first extension having a first thickness, the second extension having a second thickness, the medial portion having a third thickness that is less than the first and second thicknesses, wherein the first spacer segment having a first spacer uppermost surface is adapted to reside proximate releasably engage the second lower plate surface such that the first through hole is aligned with one of the at least one through holes in the second plate end, and the second through hole is aligned with another of the at least one through holes in the second plate end.

2. The apparatus of claim 1, wherein the first spacer segment is removably coupled to the plate by a connector.

3. The apparatus of claim 2, wherein the connector comprises a first portion on the first spacer segment and a second portion on the plate.

4. The apparatus of claim 3, wherein the first portion comprises a plurality of resilient extending portions and the second portion comprises at least an internal wall such that the plurality of resilient extending portions form a friction fitting with the internal wall.

5. The apparatus of claim 3, wherein the first portion comprises an extending portion with a first limiting wall and the second portion comprises at least an internal wall with a second limiting wall such that the first and second limiting walls cooperatively engage to from a snap fitting.

6. The apparatus of claim 2, wherein the connector comprises a screw having external threads and bore having internal threads.

7. The apparatus of claim 2, wherein the connector is selected from the group of connectors consisting of a keyed connector, a tenon and mortise, a splined connector, an adhesive, or a dovetail.

8. The apparatus of claim 1, comprising at least a second spacer segment removably coupled to the first spacer end.

9. The apparatus of claim 8, wherein the first spacer segment is disposed between the plate and the second spacer segment.

10. The apparatus of claim 1, wherein at least one of the first and second thicknesses is adapted to extend across a gap between the lower plate surface and the boney segment.

11. The apparatus of claim 1, wherein the first spacer end includes a fourth thickness that is adapted to provide indexing for at least one of the fasteners.

12. The apparatus of claim 1, wherein the first spacer end includes a fourth thickness that is adapted to provide indexing for at least one of the fasteners and wherein at least one of the first and second thickness is adapted to extend across a gap between the second plate surface and the boney segment.

13. The apparatus of claim 1, wherein the first spacer segment comprises a buttress extending from the second spacer end in a direction away from the first spacer end.

14. The apparatus of claim 1, wherein the plate comprises a side edge extending between the upper plate surface and the lower plate surface and the uppermost segment comprises a ridge extending from the first spacer surface of the first spacer segment that is shaped to cooperatively engage the side edge.

15. The apparatus of claim 1, wherein the first and second extensions extend below the lower plate surface plate surface.

16. An apparatus adapted to facilitate a fusion between at least two boney segments, the apparatus comprising:
a plate longitudinally extending between a first plate end and a second plate end comprising a first plate surface having a border forming a cavity that is spaced apart from an opposing second plate surface, the plate comprising at least one through hole in the first plate end and at least one through hole in the second plate end, the first plate surface comprising a shelf portion at each through hole;
a plurality of plate securing mechanisms adapted to extend through the through holes and couple the plate to the at least two boney segments;
a single cover releasably attachable to the plate to prevent the plate securing mechanisms from dissociating from the plate, the single cover fitting in the cavity formed by the border and having a top surface that is spaced apart from an opposing bottom surface that is configured to reside proximate the first plate surface, the bottom surface comprising a circular pad structure for each shelf, the circular pad structure protruding from the bottom surface to a pad surface such that the to surface and a first portion of the bottom surface have a first thickness, and the to surface and the pad surface have a second thickness that is greater than the first thickness; and
a cover securing mechanism to releasably attach the single cover to the first plate surface.

17. The apparatus of claim 16, wherein the cover securing, mechanism includes an opening in the cover extending from the top surface to the bottom surface, a bore having internal threads in the first plate surface, and a set screw with external threads corresponding to the internal threads of the bore.

18. The apparatus of claim 17, wherein the top surface has a relief surface sized to cooperatively engage a head of the set screw such that the head of the set screw is flush with the top surface.

19. The apparatus of claim 16, wherein the plate has a third thickness and the border has a fourth thickness that is greater than the third thickness, the third thickness being between the first plate end and the second plate end.

20. The apparatus of claim 19, wherein the plate has a plurality of first through holes in the first plate end and a plurality of second through holes in the second plate end and the third thickness is between at least one of the plurality of first through holes and the plurality of second through holes.

21. A method adapted to promote a fusion between at least two boney segments, the method comprising;
obtaining a plate longitudinally extending between a first plate end and a second plate end;
determining the height of a gap extending between the first plate end and a first of the at least two boney segments;
selecting between a first spacer segment and a second spacer segment, each of the first and second spacer segments having a first spacer end and an opposed second spacer end, wherein the first spacer end of the first spacer segment has a first thickness and the second spacer end of the first spacer segment has a second thickness greater than the first thickness, and wherein the first spacer end of the second spacer segment has a third thickness and the second spacer end of the second spacer segment has a fourth thickness greater than the third thickness, wherein the second thickness of the first spacer segment is different than the fourth thickness of the second spacer segment and wherein the second thickness of one of the first and second spacer segments corresponds to the height of the gap between the first plate end and the first of the at least two boney segments; and
combining the plate and the first spacer segment prior to implantation of the combined plate and first spacer segment into a body.

22. The method of claim 21 comprising:
implanting the combined plate and spacer segment into the body, such that the second thickness extends the height of the gap;

securing the combined plate and spacer segment to the body using securing mechanisms; and securing a cover to the combined plate and spacer segment to prevent the plate securing mechanisms from dissociating from the plate.

* * * * *

UNITED STATES PATENT AND TRADEMARK OFFICE
CERTIFICATE OF CORRECTION

| | | |
|---|---|---|
| PATENT NO. | : 9,119,682 B2 | Page 1 of 1 |
| APPLICATION NO. | : 13/580611 | |
| DATED | : September 1, 2015 | |
| INVENTOR(S) | : Stoll et al. | |

It is certified that error appears in the above-identified patent and that said Letters Patent is hereby corrected as shown below:

In the Claims

In column 18, line 15, in Claim 16, before "surface", delete "to" and insert --top--, therefor In column 18, line 17, in Claim 16, delete "to" and insert --top--, therefor Signed and Sealed this
Nineteenth Day of January, 2016

Michelle K. Lee
*Director of the United States Patent and Trademark Office*